(12) United States Patent
Fisher et al.

(10) Patent No.: US 9,474,461 B2
(45) Date of Patent: Oct. 25, 2016

(54) MINIATURE WIRELESS BIOMEDICAL TELEMETRY DEVICE

(75) Inventors: John H. Fisher, Cottonwood Heights City, UT (US); F. Edward Dudek, Salt Lake City, UT (US); Mark J. Lehmkuhle, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 1159 days.

(21) Appl. No.: 12/681,408

(22) PCT Filed: Oct. 2, 2008

(86) PCT No.: PCT/US2008/078616
§ 371 (c)(1),
(2), (4) Date: Apr. 14, 2010

(87) PCT Pub. No.: WO2009/046214
PCT Pub. Date: Apr. 9, 2009

(65) Prior Publication Data
US 2010/0222686 A1  Sep. 2, 2010

Related U.S. Application Data

(60) Provisional application No. 60/977,122, filed on Oct. 3, 2007.

(51) Int. Cl.
*A61B 5/00* (2006.01)
*A61B 5/0476* (2006.01)
*A61B 5/0402* (2006.01)

(52) U.S. Cl.
CPC .......... *A61B 5/0476* (2013.01); *A61B 5/0006* (2013.01); *A61B 5/0402* (2013.01); *A61B 5/4094* (2013.01)

(58) Field of Classification Search
CPC ...... H04B 5/0012; A61B 5/00; A61B 5/021; A61B 5/0402; A61B 5/0476; A61B 5/0006; A61B 5/4094; A61B 5/0215
USPC .................. 600/300, 544–545; 455/41.1
See application file for complete search history.

(56) References Cited

U.S. PATENT DOCUMENTS 3,815,109 A   6/1974  Carraway et al.
4,958,645 A   9/1990  Cadell et al.
(Continued)

FOREIGN PATENT DOCUMENTS

EP        0944414 A2    9/1999
WO    WO-03/030581 A2   4/2003

OTHER PUBLICATIONS

Liu, et al. "A Multichannel, Wireless Telemetric Microsystem for Small Animal Studies," IEEE Sensors Journal, vol. 6, No. 1, Feb. 2006.*

(Continued)

*Primary Examiner* — Navin Natnithithadha
*Assistant Examiner* — Eric Messersmith
(74) *Attorney, Agent, or Firm* — Hayes Soloway P.C.

(57) ABSTRACT

Provided herein are embodiments of a miniature wireless biomedical telemetry device along with systems and methods for its use. A miniature amplifier and transmitter allow recording of physiological signals from small animals, such as rats, mice and birds, as well as humans. The device is positioned externally and is easily replaceable, as is its battery, so surgical complications and other problem problems are minimized.

24 Claims, 26 Drawing Sheets

(56) References Cited

U.S. PATENT DOCUMENTS

| | | | | |
|---|---|---|---|---|
| 5,166,679 | A | * | 11/1992 | Vranish et al. .......... 340/870.37 |
| 5,279,305 | A | | 1/1994 | Zimmerman et al. ........ 128/731 |
| 5,914,701 | A | * | 6/1999 | Gersheneld et al. ......... 345/156 |
| 5,987,352 | A | | 11/1999 | Klein et al. |
| 6,029,084 | A | | 2/2000 | Long et al. ........................ 607/2 |
| 6,052,619 | A | | 4/2000 | John ............................ 600/544 |
| 6,132,371 | A | | 10/2000 | Dempsey et al. |
| 6,238,338 | B1 | | 5/2001 | DeLuca et al. ............... 600/300 |
| 6,315,719 | B1 | | 11/2001 | Rode et al. ................... 600/300 |
| 6,434,420 | B1 | | 8/2002 | Taheri |
| 6,609,419 | B1 | * | 8/2003 | Bankart et al. .............. 73/146.5 |
| 6,654,633 | B2 | | 11/2003 | Stengel et al. ................ 600/544 |
| 6,673,596 | B1 | | 1/2004 | Sayler et al. |
| 6,749,566 | B2 | | 6/2004 | Russ ............................ 600/300 |
| 6,968,743 | B2 | | 11/2005 | Rich et al. |
| 7,010,340 | B2 | | 3/2006 | Scarantino et al. |
| 7,091,879 | B2 | | 8/2006 | Swetlik et al. .......... 340/870.16 |
| 7,101,343 | B2 | | 9/2006 | Delalic et al. |
| 7,188,151 | B2 | | 3/2007 | Kumar et al. ................ 709/217 |
| 7,191,007 | B2 | | 3/2007 | Desai et al. |
| 7,222,054 | B2 | | 5/2007 | Geva ............................ 702/188 |
| 7,292,828 | B1 | | 11/2007 | Liu et al. ........................ 455/91 |
| 7,346,312 | B2 | | 3/2008 | Irazoqui-Pastor et al. .. 455/41.2 |
| 7,978,063 | B2 | * | 7/2011 | Baldus et al. ........... 340/539.12 |
| 2002/0099277 | A1 | | 7/2002 | Harry et al. ................... 600/301 |
| 2002/0138009 | A1 | | 9/2002 | Brockway et al. |
| 2003/0114769 | A1 | | 6/2003 | Loeb et al. |
| 2003/0233250 | A1 | | 12/2003 | Joffe et al. ........................ 705/2 |
| 2004/0073127 | A1 | | 4/2004 | Istvan et al. |
| 2004/0111130 | A1 | | 6/2004 | Hrdlicka et al. ................ 607/48 |
| 2005/0054941 | A1 | | 3/2005 | Ting et al. |
| 2005/0251002 | A1 | | 11/2005 | Istvan et al. |
| 2005/0251004 | A1 | | 11/2005 | Istvan et al. |
| 2006/0007796 | A1 | | 1/2006 | Merilainen |
| 2006/0020300 | A1 | | 1/2006 | Nghiem et al. ................. 607/60 |
| 2006/0063488 | A1 | * | 3/2006 | Hraby et al. ................. 455/41.1 |
| 2006/0110049 | A1 | | 5/2006 | Liang et al. |
| 2006/0173259 | A1 | | 8/2006 | Flaherty et al. .............. 600/331 |
| 2007/0085690 | A1 | | 4/2007 | Tran |
| 2007/0173732 | A1 | * | 7/2007 | Causevic et al. ............. 600/544 |
| 2007/0244374 | A1 | * | 10/2007 | Vyssotski et al. ............. 600/301 |
| 2008/0091090 | A1 | * | 4/2008 | Guillory et al. .............. 600/301 |
| 2009/0024044 | A1 | | 1/2009 | Virtanen et al. |
| 2011/0098593 | A1 | | 4/2011 | Low et al. |

OTHER PUBLICATIONS

European Extended Search Report issued Jul. 9, 2012 in application No. 08835060.8- 2319/2207471 PCT/US2008078616 (6 pgs).
Bastlund et al. "Measurement of cortical and hippocampal epileptiform activity in freely moving rats by means of implantable radiotelemetry." J Neurosci Methods. 2004, 138(1-2):65-72. PMID: 15325113.
Bertram E.H. "Functional anatomy of spontaneous seizures in a rat model of limbic epilepsy." Epilepsia. 1997, 38(1):95-105. PMID: 9024190.
Bertram et al. "The evolution of a rat model of chronic spontaneous limbic seizures." Brain Res. 1994, 661(1-2):157-62. PMID: 7834366.
Bertram et al. "The ontogeny of seizures in a rat model of limbic epilepsy: evidence for a kindling process in the development of chronic spontaneous seizures." Brain Res. Oct. 22, 1993;625(2):295-300. PubMed PMID: 8275310.
Buckmaster et al. "Neuron loss, granule cell reorganization and functional changes in the dentate gyrus of epileptic kainate-treated rats." J. Comp. Neurol. 1997, 385:385-404.
Cheney et al. "Wireless, in Vivo Neural Recording using a Custom Integrated Bioamplifier and the Pico System," 3rd Int'l IEEE Embs Conf. on Neural Engineering. 2007, 19-23.
Dudek et al. "Kainate-induced status epilepticus: A chronic model of acquired epilepsy." In: Models of Seizures and Epilepsy. Amsterdam, Netherlands: Elsevier, 2006, 415-432.
Farshchi et al. "A TinyOS-based wireless neural interface." Conf Proc IEEE Eng Med Biol Soc. 2004, 6:4334-7.
Farshchi et al. "A TinyOS-enabled MICA2-based wireless neural interface." IEEE Trans Biomed Eng. 2006, 53(7):1416-24.
Farshichi et al. "An Embedded System Architecture for Wireless Neural Recording," 3rd Int'l IEEE EMBS Conf. on Neural Engineering. 2007, 326-332.
Frey, L.C. "Epidemiology of posttraumatic epilepsy: a critical review." Epilepsia, 2003, 44(Supp 10): 11-17.
Fromherz, P. "Neuroelectronic Interfacing: Semiconductor Chips with Ion Channels, Nerve Cells and Brain," Nanoelectronics and Information Technology, 2003, 781-810.
Garga et al. "Posttraumatic epilepsy: A major problem in desperate need of major advances." Epilepsy Currents, 2006, 6:1-5.
Hellier et al. "Assessment of inhibition and epileptiform activity in the septal dentate gyrus of freely-behaving rats during the first week after kainate treatment." J. Neurosci. 1999, 19:10053-10064.
Hellier et al. "Chemoconvulsant model of chronic spontaneous seizures." Curr Protoc Neurosci. 2005, Chapter 9:Unit 9.19. PMID: 18428628.
Hellier et al. "Recurrent spontaneous motor seizures after repeated low-dose systemic treatment with kainate: assessment of a rat model of temporal lobe epilepsy." Epilepsy Res. 1998, 31:73-84.
Hutzler et al. "High Resolution Multitransistor Array Recording of Electric Field Potentials in Cultured Brain Slices," J. Neurophysiology, Sep. 2006, 96:1638-1645.
Irazoqui et al. "Recording brain activity wirelessly. Inductive powering in miniature implantable neural recording devices." IEEE Eng Med Biol Mag. 2005, 24(6):48-54.
Kadam et al. "Neuropathological features of a rat model for perinatal hypoxic-ischemic encephalopathy with associated epilepsy." J. Comp. Neurol. 2007, 505:716-737.
Nuyujukian et al. "A TinyOS-based wireless neural interface." Undergraduate Research Program. University of California, Los Angeles—Electrical Engineering Department. Undated reference.
Stables et al. "Therapy discovery for pharmacoresistant epilepsy and for disease modifying therapeutics: Summary of the NIH/NINDS/AES Models II Workshop." Epilepsia. 2003, 44:1472-1478.
Vespa et al. "Increased incidence and impact of nonconvulsive and convulsive seizures after traumatic brain injury as detected by continuous electroencephalogephic monitoring." J. Neurosurg. 1999, 91: 750-760.
Vespa, P. "Continuous EEG monitoring for the detection of seizures in traumatic brain injury, infarction, and intracerebral hemorrhage: To detect and protect." J. Clin Neurophysiol. 2006, 22: 99-106.
White et al. "Efficient unsupervised algorithms for the detection of seizures in continuous EEG recordings from rats after brain injury." J Neurosci Methods. 2006, 152(1-2):255-66.
Williams et al. "Epilepsy and synaptic reorganization in a perinatal rat model of hypoxia-ischemia." Epilepsia. 2004, 45:1210-1218.
Williams et al. "The use of radiotelemetry to evaluate electrographic seizures in rats with kainate-induced epilepsy." J Neurosci Methods. 2006, 155(1):39-48.
Wise et al. "High Density Electronic Interfaces to the Nervous System," IEEE Proceedings, 2004, 92:76-97.
Yates et al. "A Key Power Trade-Off in Wireless EEG Headset Design," 3rd Int'l IEEE EMBS Conf. on Neural Engineering. 2007, 453-456.
International Search Report issued on Dec. 3, 2008 for Intl. App. No. PCT/US08/078616 filed Oct. 2, 2008 (Inventor—Fisher).
Written Opinion issued on Dec. 3, 2008 for Intl. App. No. PCT/US08/078616 filed Oct. 2, 2008 (Inventor—Fisher).
International Preliminary Report on Patentability issued on Apr. 7, 2010 for Intl. App. No. PCT/US08/078616 filed Oct. 2, 2008 (Inventor—Fisher).
EPO Communication in corresponding EP Patent Application No. 08 835 060.8 dated Jul. 22, 2016, 6 pgs.

* cited by examiner

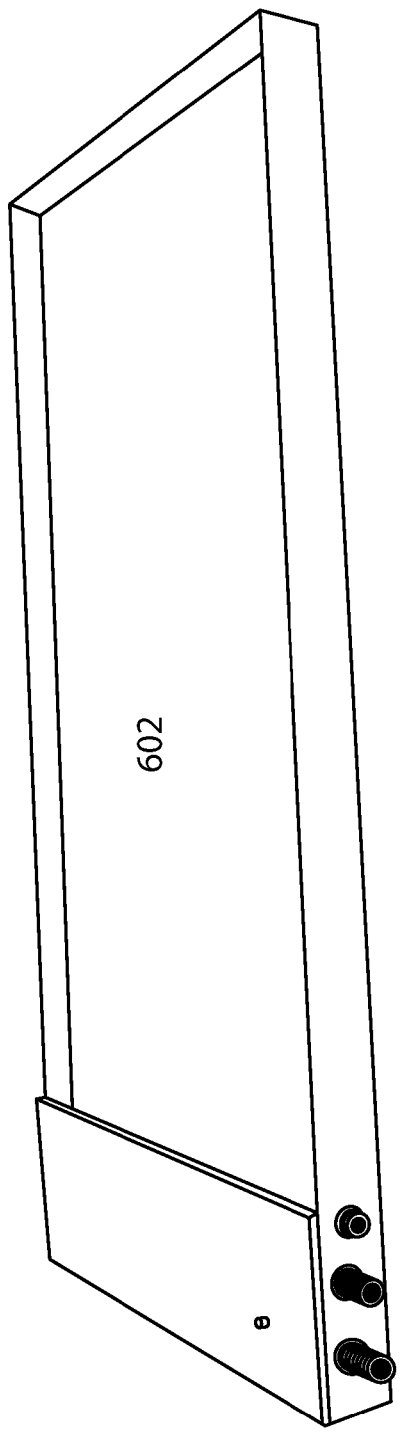

MINIATURE WIRELESS BIOMEDICAL TELEMETRY DEVICE

CROSS REFERENCE TO RELATED APPLICATION

This application claims benefit of and priority to U.S. Provisional Patent Application No. 60/977,122 filed Oct. 3, 2007, which is fully incorporated herein by reference and made a part hereof.

This invention is made with government support under grant numbers NS045144, NS049620, NS042359, DC004390 and DC006876 awarded by National Institute of Health. The government has certain rights to this invention.

BACKGROUND

1. Field of the Invention

The embodiments described herein relate to biomedical telemetry devices, and more particularly to miniature wireless biomedical telemetry devices and methods of their use.

2. Background

The untethered monitoring of disease and injury in animal models, primarily in rats and mice, and comparable monitoring of humans in cases of suspected or demonstrated disease or injury, is important for the development of new therapies, determining markers for seizures or other acute events, and the development and application of treatment protocols.

Currently, monitoring physiological signals such as electroencephalogram (EEG), electrocardiogram (ECG), blood pressure, etc. requires cumbersome monitoring systems that generally involve surgical implantation and/or have limited monitoring time because of power consumption and, in humans, require expensive hospital stays with numerous electrodes, and as a minimum, result in limited mobility and otherwise prevent a normal way-of-life.

Epilepsy is the second most prevalent neurological disorder with over 50 million people affected worldwide. Nearly three million individuals in the U.S. have epilepsy, and over 30% are refractory to treatment with antiepileptic drugs (AEDs). The medical, psychological, sociological and financial implications of refractory epilepsy can be devastating for both the patient and their families. Seizures can be debilitating and result in major irreversible morbidity, often with long-term consequences that may include brain damage from recurrent seizures, seizure-induced injuries and accidents associated with loss of consciousness, impairment of memory, and even death. The personal consequences of refractory epilepsy may include the adverse effects of AEDs, strained personal and family relations, and the inability to obtain and hold meaningful employment or even a driver's license. Thus, there is a need for better approaches and new technologies for discovering novel therapies for intractable epilepsy.

One of the most widely used techniques for recording epileptic seizures is the EEG. This technique remains the mainstay to diagnose epilepsy, and to help localize the seizure onset zone in people with intractable epilepsy. As in the clinical diagnosis of the epilepsies, the EEG has become indispensable for translational research in animal models of both genetic and acquired epilepsy. This technique is also widely used to provide fundamental information about the mechanisms of sleep and to diagnose sleep disorders. For some research, "wired" or "tethered" recordings are quite acceptable and can be done in adult rats for weeks at a time. However, electrical noise, movement artifacts, and the risk that tethered animals will injure themselves by pulling on the cable have led to the need for radio-telemetry over the last several years. Current "wireless" systems, however, often involve extensive surgery to implant the transmitter and battery system, an expensive and time-intensive process. Other systems use a relatively large and awkward "backpack" on the animal, which causes animal stress similar to a tether.

Further, acquired epilepsy (i.e., after brain injury, of many possible types) affects up to about 3 percent of the human population, and acute seizures after various forms of brain injury impact a much higher proportion. For example, post-traumatic epilepsy affects up to about 53 percent of adults suffering moderate to severe traumatic brain injury (TBI). Importantly, seizures early after TBI, similar to stroke, are associated with increased injury and poorer outcomes. Thus, optimal acute therapy for TBI victims and other individuals with brain injuries includes prompt seizure detection and effective therapy leading to seizure cessation. Continuous EEG monitoring reveals that roughly 25 percent of adults suffering moderate or severe TBI exhibit electrographic seizures, despite therapeutic levels of anticonvulsive medications. Nearly 60 percent of post-traumatic seizures in adults suffering severe TBI are non-convulsive seizures and can be detected only by EEG monitoring.

Aggressive, monitor-guided, early anti-seizure medical therapy may mitigate secondary brain injury after TBI and reduce the probability and severity of subsequent cognitive deficits or post-traumatic epilepsy. Ideally, EEG monitoring would be initiated as soon as possible after TBI, in order to detect non-convulsive seizures and guide anti-seizure therapy in the transport or pre-hospital setting. Reliable EEG recording during medical transport or field care will require a small device that can be properly positioned on the head quickly and lacks cumbersome cables or receivers. Unfortunately, an easy-to-use, telemetric, portable recording device is not currently available.

What are needed, therefore, are devices and methods of use that overcome challenges found in the current state of the art, some of which are described above.

SUMMARY

Provided herein are embodiments of a miniature wireless biomedical telemetry device along with systems and methods for its use. A miniature amplifier and transmitter allow recording of physiological signals from small animals, such as rats, mice and birds, as well as humans. The device is positioned externally and is easily replaceable, as is its battery, so surgical complications and other challenges are minimized.

In one aspect, a miniature, wireless, capacitive-coupled biomedical telemetry device and system having long-life and minimally-invasive surgical procedures configured to monitor physiological signals (e.g., EEG, ECG, blood pressure, etc.) as well as environmental sensors (e.g., temperature, pressure, etc.) is described.

In another aspect, a miniature, wireless, biomedical telemetry device and system comprised of a transmitter, electrodes and power source integrated on a single substrate having long-life and configured to monitor physiological signals (e.g., EEG, ECG, blood pressure, etc.) as well as environmental sensors (e.g., temperature, pressure, etc.) is described.

In yet another aspect, described herein are embodiments of a miniature telemetry system to permit continuous, uninterrupted EEG recordings; this will be accomplished with a capacitive-coupled telemetry system that uses commonly-available batteries (e.g., watch batteries) as a power source, which would allow straight-forward replacement of either the battery or the entire unit without invasive surgery.

In one aspect the power source for the telemetry unit can be one or more photodiodes.

In another aspect, the wireless telemetry device can comprise a multi-channel transmitter such as, for example, a pulse-width modulated (PWM) two-channel transmitter.

Although the most pressing need is probably for research and clinical care during and after various forms of brain injury, embodiments according to the present invention have potential use in many other experimental animal and human clinical studies. These include, but are not limited to anti-epileptic drug testing and optimization in both animal and human studies, research and care of migraine headache, and analyses of sleep disorders, including development and optimization. Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems:

FIGS. 6-7A illustrate embodiments of a standard rat cage modified for capacitive-coupling of the transmitter and receipt of physiological data;

DETAILED DESCRIPTION

Figure 1:
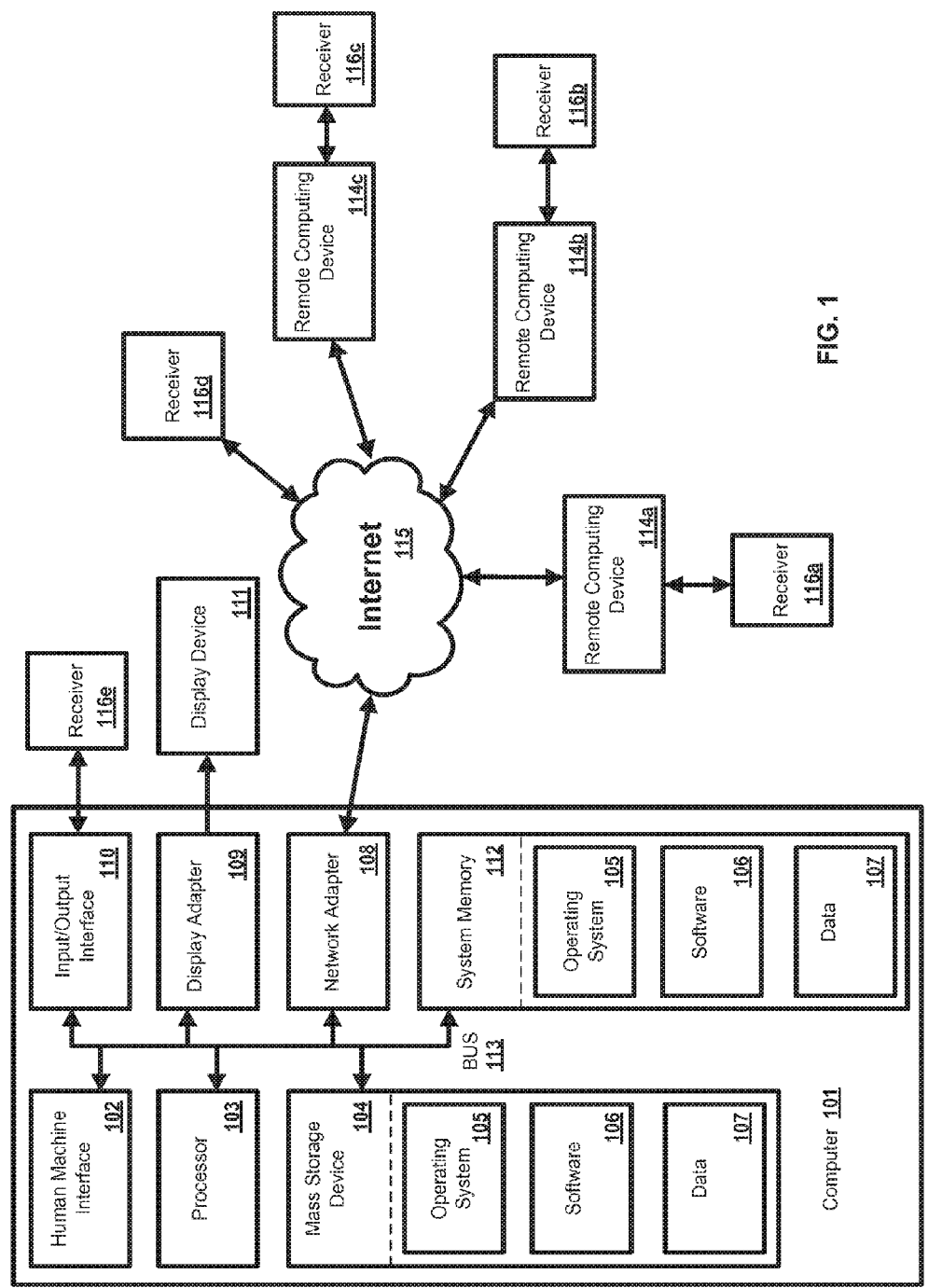
FIG. 1 is an exemplary computing device that can be used according to aspects of the present invention for processing and analysis of the received information or performing any other needed computing/processing functions.

Before the present methods and systems are disclosed and described, it is to be understood that the methods and systems are not limited to specific synthetic methods, specific components, or to particular compositions, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

"Exemplary" means "an example of" and is not intended to convey a preferred or ideal embodiment. Further, the phrase "such as" as used herein is not intended to be restrictive in any sense, but is merely explanatory and is used to indicate that the recited items are just examples of what is covered by that provision.

Other definitions used herein include:
A/D: analog-to-digital;
dbm: decibel power level in milliwatts;
EEG: electroencephalogram;
FCC: Federal Communication Commission;
FM: frequency modulation;
PC: personal computer;
RF: radio-frequency;
PWM: pulse-width modulation; and
USB: universal serial bus.

The present methods and systems may be understood more readily by reference to the following detailed description of preferred embodiments and the Examples included therein and to the Figures and their previous and following description.

In one embodiment described herein is a micro-transmitter comprised of a physiological amplifier controlling a pulse-width (or frequency) modulation oscillator. The recording input is two leads connected to an AC-coupled amplifier (or DC for pressure and other sensor measurements). In one aspect, the amplitude of the physiological signal modulates the pulse width of a square-wave oscillator, which is transmitted via capacitive coupling to the antenna(s). Advantageously, this process is performed with one miniaturized device so that it can be fastened directly to the head (or elsewhere) of the animal. In one aspect, the miniaturized device is self-contained and includes a power source such as a small battery. In one aspect, the device presently operates from a single 1.4 V zinc air cell, and power consumption is <3 µA, providing an estimated >270 days of operation with a #5 cell. In another aspect, photodiodes, as are known in the art, are used as the power source. A high-impedance receiver picks up, amplifies, and provides filtering of the signal. In one aspect, the signal can be leveled via an automatic gain control (AGC). An integrator (or a frequency-to-voltage converter) and a band-pass filter recover the original AC signal from the transmitter.

In another aspect, the device is coupled with a radio frequency (RF) transmitter for wirelessly transmitting monitored data to a remote receiver.

Figure 5:
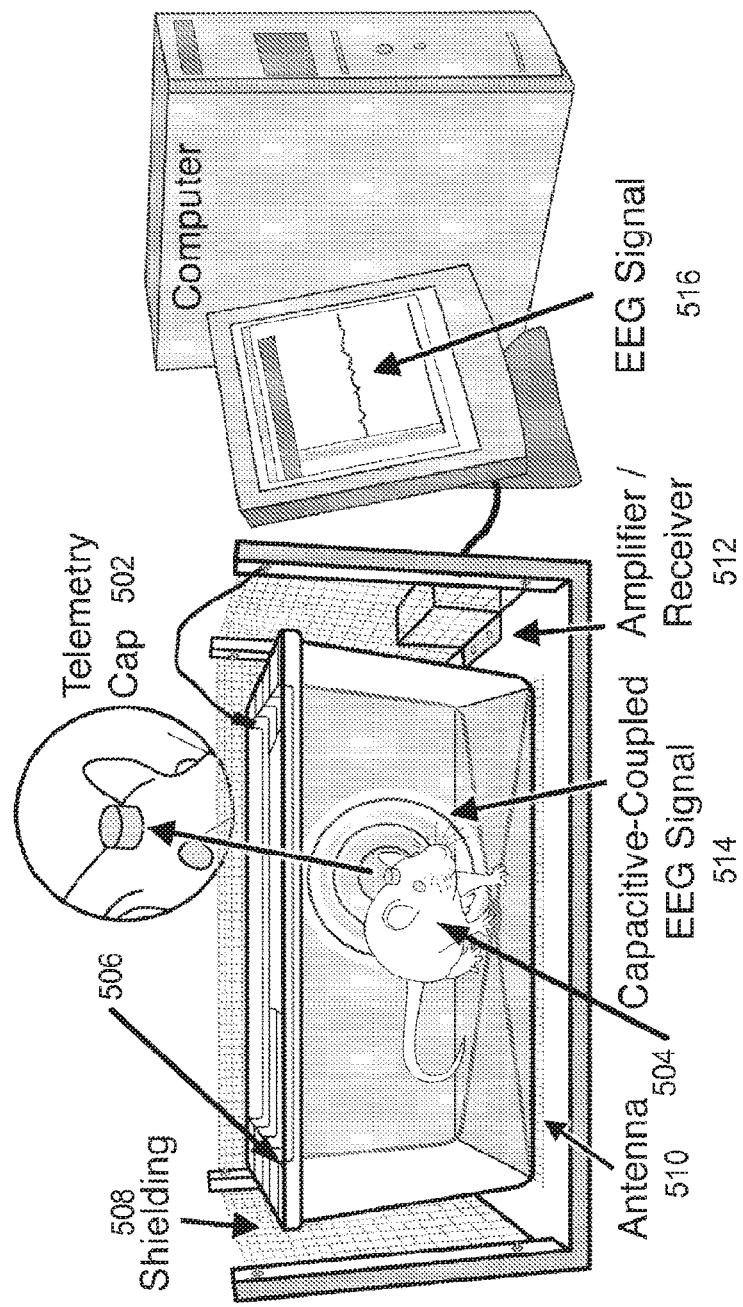
FIG. 5 is a schematic diagram of an embodiment of a miniature EEG telemetry system.

In some instances, the receiver can be operably connected with a computing device, such as that shown in FIGS. 1 and 5 for processing and analysis of the received information or performing any other needed computing/processing functions.

Functions as described herein can be performed by software, hardware, or a combination of software and hardware. A unit can be software, hardware, or a combination of software and hardware. The units can comprise the Analysis Software 106 as illustrated in FIG. 1 and described below. In one exemplary aspect, the units can comprise a computer 101 as illustrated in FIG. 1 and described below.

FIG. 1 is a block diagram illustrating an exemplary operating environment for performing the disclosed method. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the system and method comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed system and method can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed method can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the system and method disclosed herein can be implemented via a general-purpose computing device in the form of a computer 101. The components of the computer 101 can comprise, but are not limited to, one or more processors or processing units 103, a system memory 112, and a system bus 113 that couples various system components including the processor 103 to the system memory 112. In the case of multiple processing units 103, the system can utilize parallel computing.

The system bus 113 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI) bus also known as a Mezzanine bus. The bus 113, and all buses specified in this description can also be implemented over a wired or wireless network connection and each of the subsystems, including the processor 103, a mass storage device 104, an operating system 105, analysis software 106, received data 107, a network adapter 108, system memory 112, an Input/Output Interface 110, a display adapter 109, a display device 111, and a human machine interface 102, can be contained within one or more remote computing devices 114a,b,c at physically separate locations, connected through buses of this form, in effect implementing a fully distributed system.

The computer 101 typically comprises a variety of computer readable media. Exemplary readable media can be any available media that is accessible by the computer 101 and comprises, for example and not meant to be limiting, both volatile and non-volatile media, removable and non-removable media. The system memory 112 comprises computer readable media in the form of volatile memory, such as random access memory (RAM), and/or non-volatile memory, such as read only memory (ROM). The system memory 112 typically contains data such as received data 107 and/or program modules such as operating system 105 and analysis software 106 that are immediately accessible to and/or are presently operated on by the processing unit 103.

In another aspect, the computer 101 can also comprise other removable/non-removable, volatile/non-volatile computer storage media. By way of example, FIG. 1 illustrates a mass storage device 104 which can provide non-volatile storage of computer code, computer readable instructions, data structures, program modules, and other data for the computer 101. For example and not meant to be limiting, a mass storage device 104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 104, including by way of example, an operating system 105 and analysis software 106. Each of the operating system 105 and analysis software 106 (or some combination thereof) can comprise elements of the programming and the analysis software 106. Received data 107 can also be stored on the mass storage device 104. Received data 107 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 101 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the processing unit 103 via a human machine interface 102 that is coupled to the system bus 113, but can be connected by other interface and bus structures, such as a parallel port, game port, an IEEE 1394 Port (also known as a Firewire port), a serial port, or a universal serial bus (USB).

In yet another aspect, a display device 111 can also be connected to the system bus 113 via an interface, such as a display adapter 109. It is contemplated that the computer 101 can have more than one display adapter 109 and the computer 101 can have more than one display device 111. For example, a display device can be a monitor, an LCD (Liquid Crystal Display), or a projector. In addition to the display device 111, other output peripheral devices can comprise components such as speakers (not shown) and a printer (not shown) which can be connected to the computer 101 via Input/Output Interface 110.

The computer 101 can operate in a networked environment using logical connections to one or more remote computing devices 114*a,b,c*. By way of example, a remote computing device can be a personal computer, portable computer, a server, a router, a network computer, a peer device or other common network node, and so on. Logical connections between the computer 101 and a remote computing device 114*a,b,c* can be made via a local area network (LAN) and a general wide area network (WAN). Such network connections can be through a network adapter 108. A network adapter 108 can be implemented in both wired and wireless environments. Such networking environments are conventional and commonplace in offices, enterprise-wide computer networks, intranets, and the Internet 115.

For purposes of illustration, application programs and other executable program components such as the operating system 105 are illustrated herein as discrete blocks, although it is recognized that such programs and components reside at various times in different storage components of the computing device 101, and are executed by the data processor(s) of the computer. An implementation of analysis software 106 can be stored on or transmitted across some form of computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any method or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

Embodiments according to the present invention of the device are miniature, so it can be placed externally on rats, mice, birds or other small laboratory animals with quick and straight-forward surgical procedures. In one aspect, the bandwidth is 0.1-2.78 kHz (or DC for pressure and other measurements), which is suitable for most physiological signals. Other frequencies are contemplated within the scope of the invention as faster integrated circuits (IC's) would provide a higher frequency response (e.g., 20 kHz) to allow recording of action potentials, but can reduce battery life. Because the device is positioned externally and the system is shielded, it requires far less power than conventional radiotelemetry systems, so the power source is also much smaller than is used for other telemetry devices. Because the power source (e.g., battery) is smaller, it too is located externally rather than being implanted in the animal, so it can be replaced easily. If the power source is a battery, then the batteries are generally inexpensive (i.e., watch batteries, hearing-aid batteries, etc.). Alternative to the use of replaceable batteries, surface-mounted photodiodes using infrared illumination can be used with the purpose of providing a continuous power source that does not need to be changed or replaced. Embodiments of this device allow prolonged and continuous wireless recording of physiological signals.

Figure 2A:
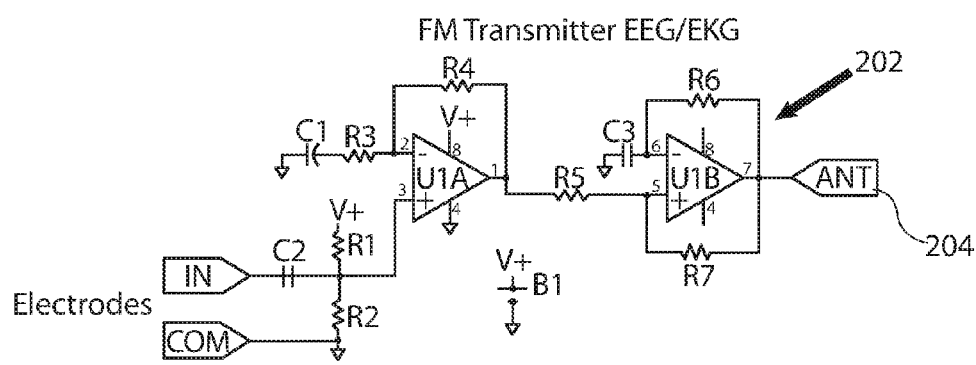
FIGS. 2A and 2B illustrate embodiments of transmitters that are small enough to mount externally on the head of a laboratory rat, mouse, or other small animal and that is able to transmit physiological signals according to an aspect of the present invention.
Figure 2B:
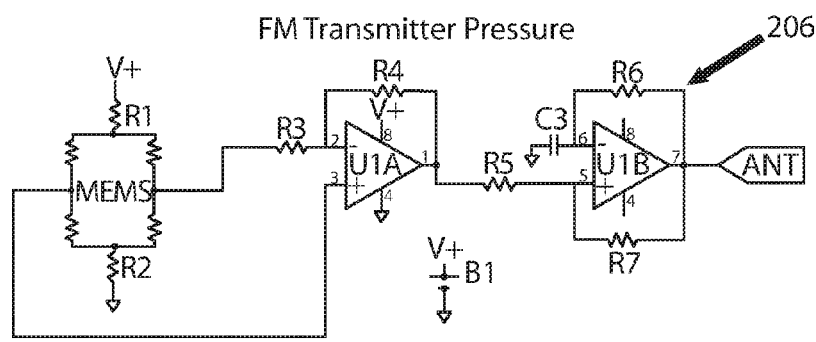

In one embodiment, a transmitter (FIGS. 2A and 2B) that is small enough to mount externally on the head of a laboratory rat, mouse, or other small animal and that is able to transmit physiological signals continuously for a year or longer is described. FIG. 2A illustrates an embodiment of a FM transmitter 202 for receiving information from EEG or ECG electrodes, modulating the information, and transmitting the modulated information to a receiver. The antenna of the transmitter is capacitively coupled with the antenna of the receiver. The physiological signals can either be electrophysiological recordings (EEG, ECG, etc.) or signals from a transducer (e.g., air or blood pressure). In one aspect, implantable recording electrodes (for example, stainless steel 0.005" wire) can be used for EEG measurement. However, it should be appreciated that any biological/medical transducer can be used with this transmitter system. For example, this system should be useful for monitoring slowly changing signals, such as temperature changes, in organisms ranging from small animals like reptiles in biological and ecological research to college and professional athletes engaged in competitive activities. High-frequency signals, most notably action potentials, can also be recorded in a research or clinical setting from lab animals and human patients by simply altering the frequency response of the amplifier in the transmitter. For example, FIG. 2B illustrates a transmitter 206 than can be used to monitor, modulate and transmit a signal related to an environmental condition such as atmospheric pressure or temperature. In one aspect, the transmitter operates from, for example, a single "#5" 1.4 volt zinc air cell and is designed using a 600 nA per channel dual operational amplifier. The low-power design of the transmitter combined with "electric field" capacitive coupling to a high-impedance receiver (FIGS. 3A and 3B) is a basis for an embodiment of the device.

One exemplary embodiment of the miniaturized device comprising a transmitter and a power source such as a 1.4 V zinc air cell has a volume of less than 1 cc, for example about 0.64 cc, and a weight of less than 1 gram. For example, one embodiment weighs about 0.8 grams, with the power source (e.g., battery). The small weight and volume makes the miniaturized device suitable for mounting on the head or body of a rat, mouse, or other laboratory animal. The low-profile design reduces stress on the animal's headcap and provides little interference with movement of the animal.

Animal Containment for Capacitive Coupling

In one aspect, because of capacitive coupling between the antenna of the transmitter and the ground plane, the animal subject must remain oriented between the antenna and ground plane, which the containment cage provides. The maximum distance between the antenna and ground plane is also controlled, and the subject should not be allowed to cover the antenna. In one aspect, the antenna is isolated from external capacitive loads by a capacitive isolation shield (i.e., driven shield) because of the capacitance between the transmitter and receiver antenna is so small. Because capacitive coupling is used according to one aspect, a number of animals can be monitored in parallel in neighboring cages without the risk of crosstalk.

A standard rat cage provides such an environment when placed on the receiver antennae system, as indicated in FIGS. 4-7B. FIGS. 6 and 7A illustrate an embodiment of an integrated antenna, amplifier and receiver unit 602. FIG. 7A illustrates the integrated unit of FIG. 6 as used with a standard rat cage 700.

Figure 7A:
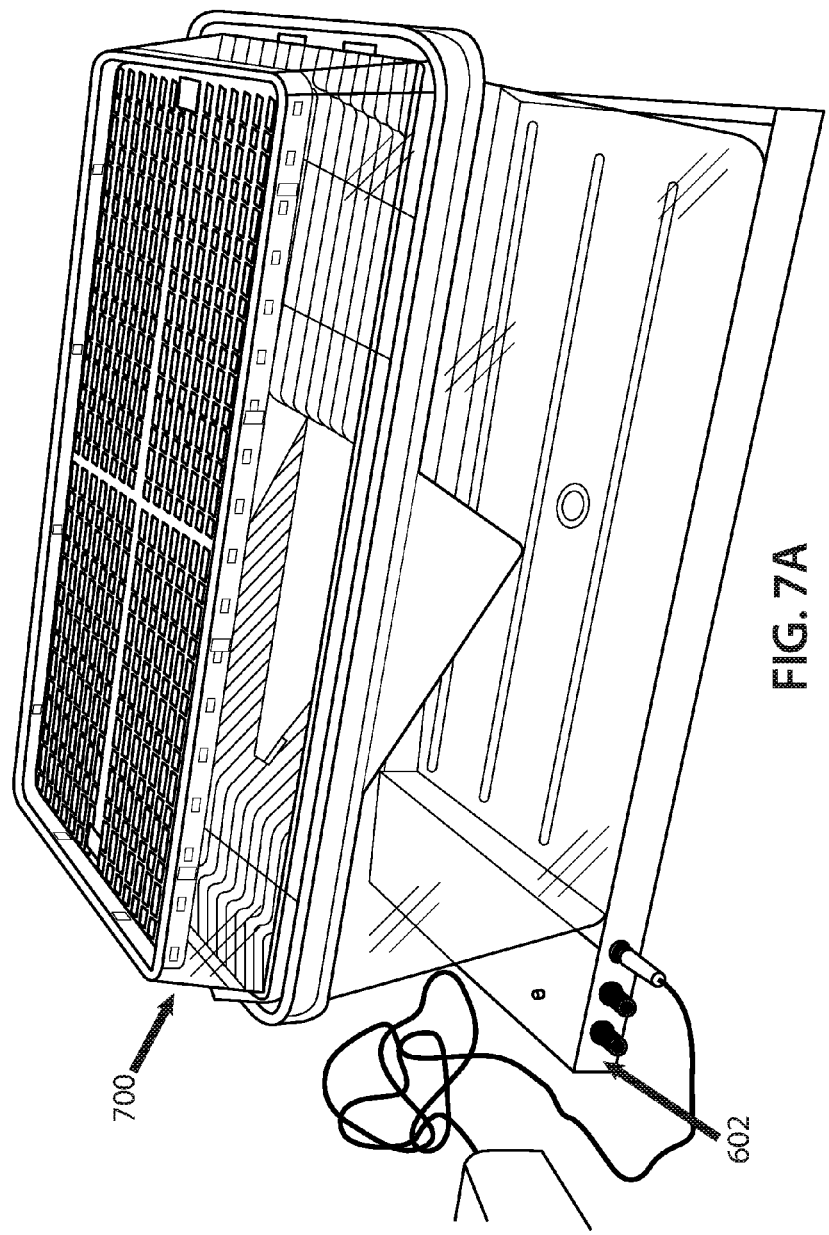
Figure 7B:
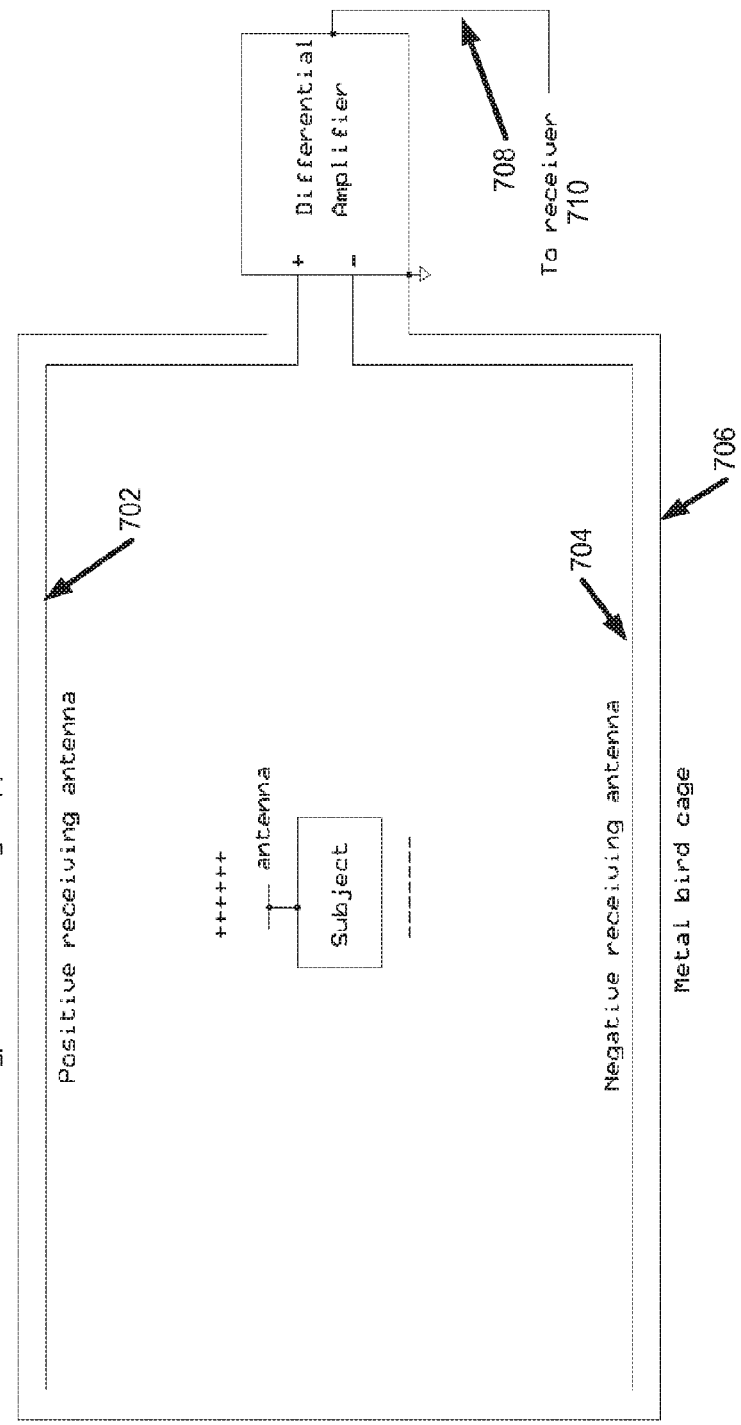
FIGS. 7B illustrates an embodiment of a cage (e.g., a bird cage) having multiple antenna(s) such that a differential input in the FM receiver then provides a constant signal as the subject moves from one antenna toward the other.

In another aspect, a differential antenna system is utilized. In larger animal containers with subjects that move in three dimensions such as birds, the receiving distance to a single antenna can be exceeded. One solution is the use of two antennas, one 702 on top and one 704 on the bottom of the container 706, as shown in FIG. 7B. A differential input 708 to the FM receiver 710 then provides a constant signal as the subject moves from one antenna toward the other. It is also contemplated that complex containers can utilize multiple antennas (greater than two).

Transmitter

An embodiment of an FM transmitter (FIG. 2A) 202 for electroencephalogram (EEG) and electrocardiogram (ECG) operates from, for example, a 1.4 volt zinc air cell. Referring to FIG. 2A, U1A forms an AC-coupled amplifier with gain set by R4 and R3. C1 sets a low-frequency cut off pole. Resistors R1 and R2 set a voltage of ½ V+ and the signal electrode is coupled to this point through C2. Note that ½ V+ and the amplified signal are present on U1A pin 1.

U1B forms a square-wave oscillator with frequency set by R6 and C3. R7 provides positive feedback and R5 sets the trip point. Note that R5 sees ½ V+ plus a varying signal that modulates the trip point. Due to non-linear plus and minus slew rates of U1B, the trip point modulates the frequency of oscillation, which is coupled to the antennae on pin 7. U1 is selected for its extremely low current draw of 600 nA per section.

A second implementation is the FM transmitter for pressure (FIG. 2B) 206. R1 and R2 reduce the current through the MSI 1451 MEMS transducer and center the input to U1A-3 and R3 at ½ V+. The output from the MEMS bridge is amplified by U1A. U1B operates as described above. Other inputs contemplated within the scope of this invention include strain gauges, chemical transducers, microphones, light sensors, and many other types of transducers or sensors can be used as inputs.

Figure 2C:
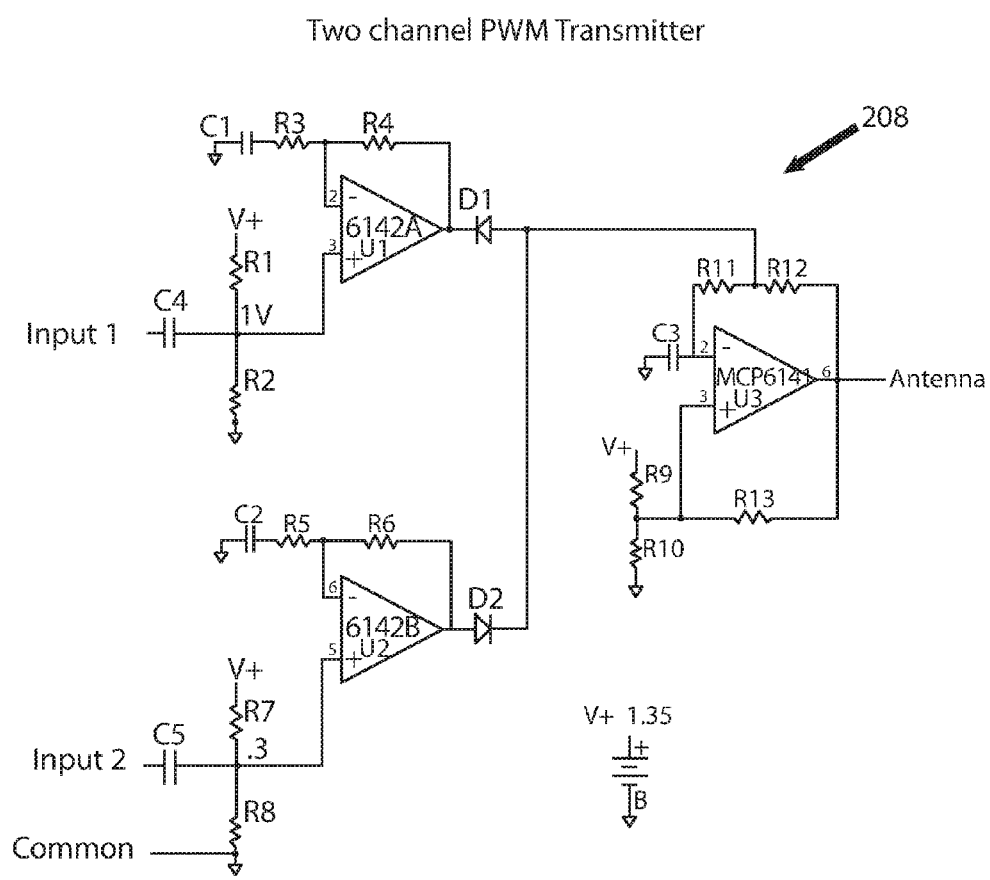
FIG. 2C illustrates an embodiment of a two channel PWM transmitter.
Figure 3A:
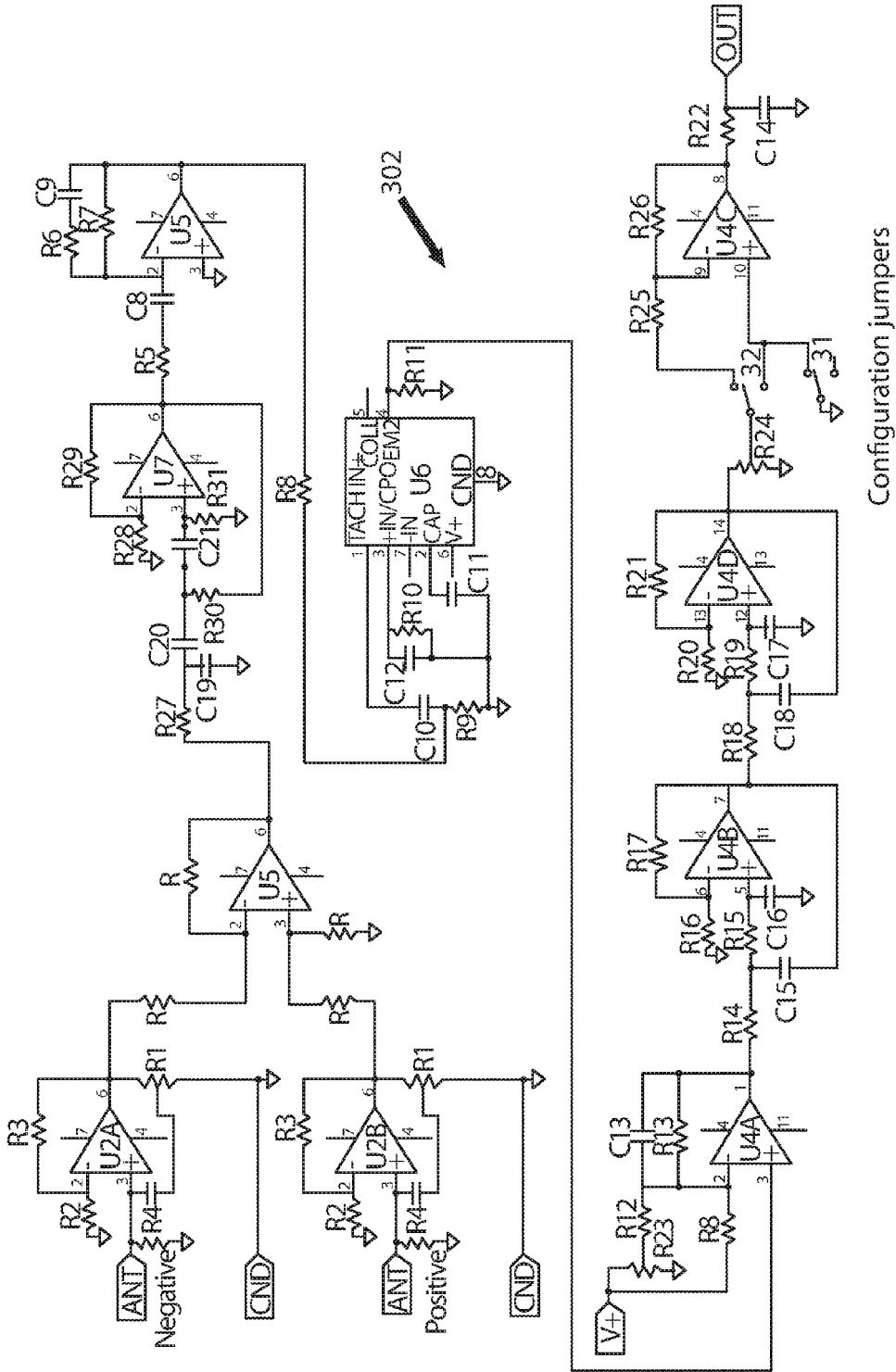
FIG. 3A illustrates one design of a differential antenna high-impedance electric field receiver that can be used with single channel transmitters (such as those shown in FIG. 2A and 2B) that provide an output voltage proportional to the frequency of the transmitter.

FIG. 2C illustrates an embodiment of a PWM two channel transmitter 208. This configuration requires minimum number of parts and low power consumption which is ideal for very small devices. U3 is a modified square wave oscillator with frequency controlled by current through R12 and R11 charging and discharging C3. U1 is an amplifier biased to clamp positive voltage at R12 via D1 and U2 is an amplifier biased to clamp negative voltage at R12 via D2. Each amplifier is modulated by an input signal and controls the positive and negative duration of U3 independently. A receiver 302 such as the one shown in FIG. 3A provides a voltage proportional to the duration of the positive swing (channel one) and the negative swing (channel two).

Figure 2D:
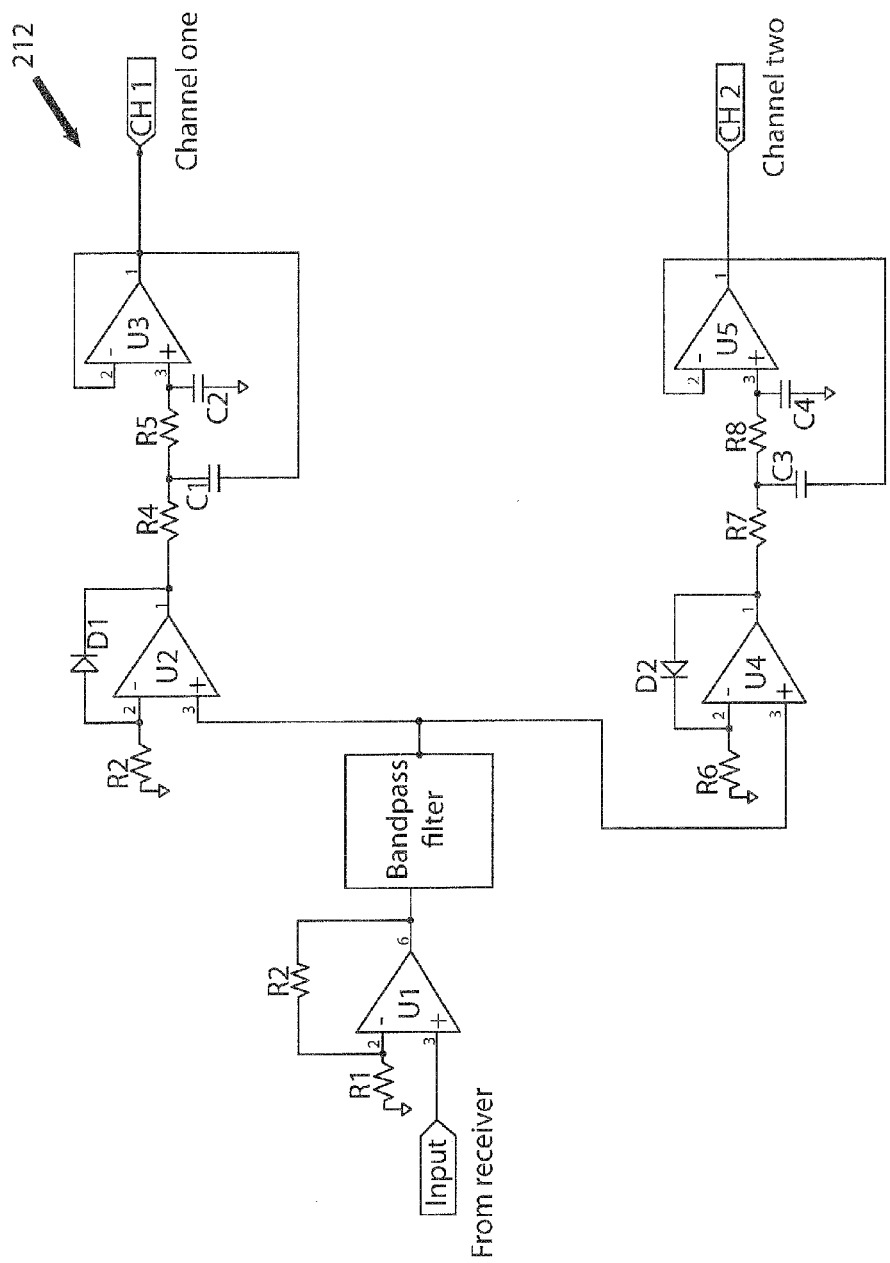
FIG. 2D illustrates an embodiment of a two channel receiver that can be used with a transmitter such as the one of FIG. 2C that provides one voltage proportional to the duration of the positive signal and one voltage proportional to the duration of the negative signal.

FIG. 2D illustrates an embodiment of a two channel receiver 212 that can be used with a transmitter such as the one of FIG. 2C that provides one voltage proportional to the duration of the positive signal and one voltage proportional to the duration of the negative signal. In FIG. 2D, a square waveform input (originating from a transmitter such as the one shown in FIG. 2C) is sent to U1, amplified, and sent through a band pass filter. Comparator U2 responds to the modulated positive duration of the waveform which is then integrated by U3 to recover the original signal. Comparator U4 responds to the modulated negative duration of the waveform which is then integrated by U5 to recover the original signal.

Power Source

Figure 2E:
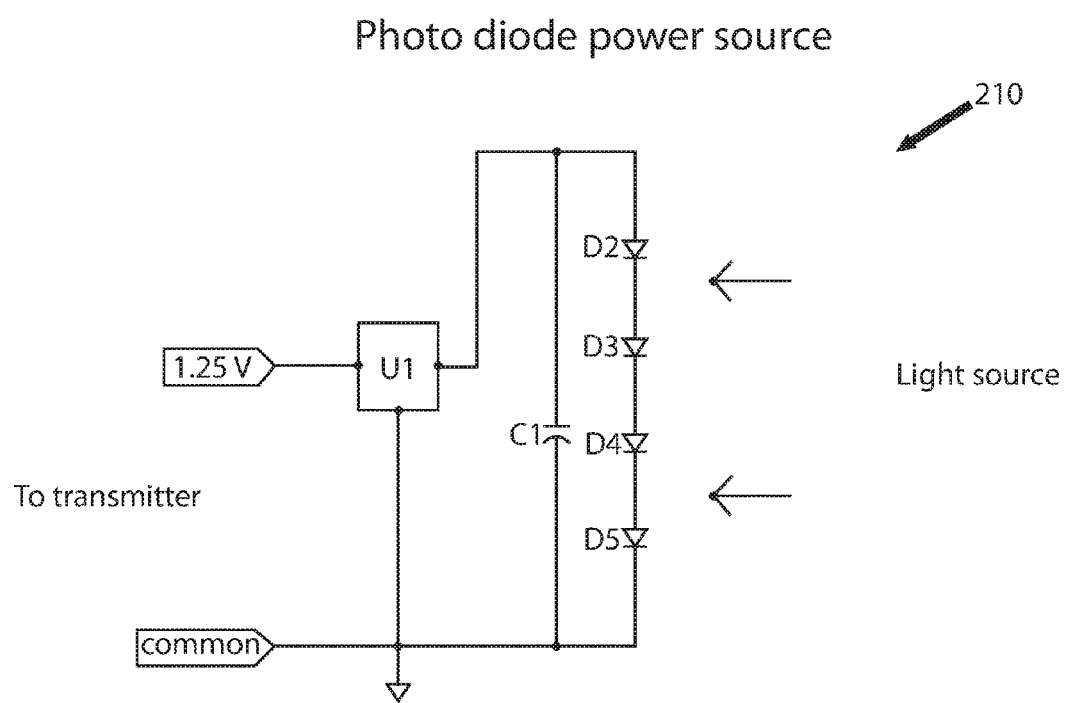
FIG. 2E illustrates an embodiment of a photodiode power source for supplying power to a transmitter.

As described herein, in one aspect the power source for the transmitter can be small, inexpensive batteries that can be replaced without surgical invasion of the subject which allows continuous or near continuous recording of information for extended periods. These batteries can be, for example, a #5, 1.4 V zinc air cell as are commonly available. In another instance, the transmitter can be powered by one or more photodiodes. An embodiment of a photodiode power source 210 is shown in FIG. 2E. Some experiments require that a signal be recorded for long periods of time. It is therefore desirable that a transmitter of these signals operate continuously and indefinitely. Because of the extremely low power requirement (<1.5 micro amps at 1.25 volts) of transmitter embodiments described herein, such transmitters can be powered by a small array of surface mount photodiodes (D2, D3, D4 and D5). A typical photo diode operating in the 940 nanometer range can produce about 0.6 volts at about 10 micro amps. Four diodes connected in series to a storage capacitor will provide about 2.4 volts to a voltage regulator U1, which draws about 3.9 micro amps. The regulator U1 provides a stable 1.25 volts for the transmitter. The total power drain is about 1.5+3.9=5.4 micro amps, well within the range of small surface mount photodiodes under typical 940 nanometer illumination.

FM Receiver/Converter

Figure 3B:
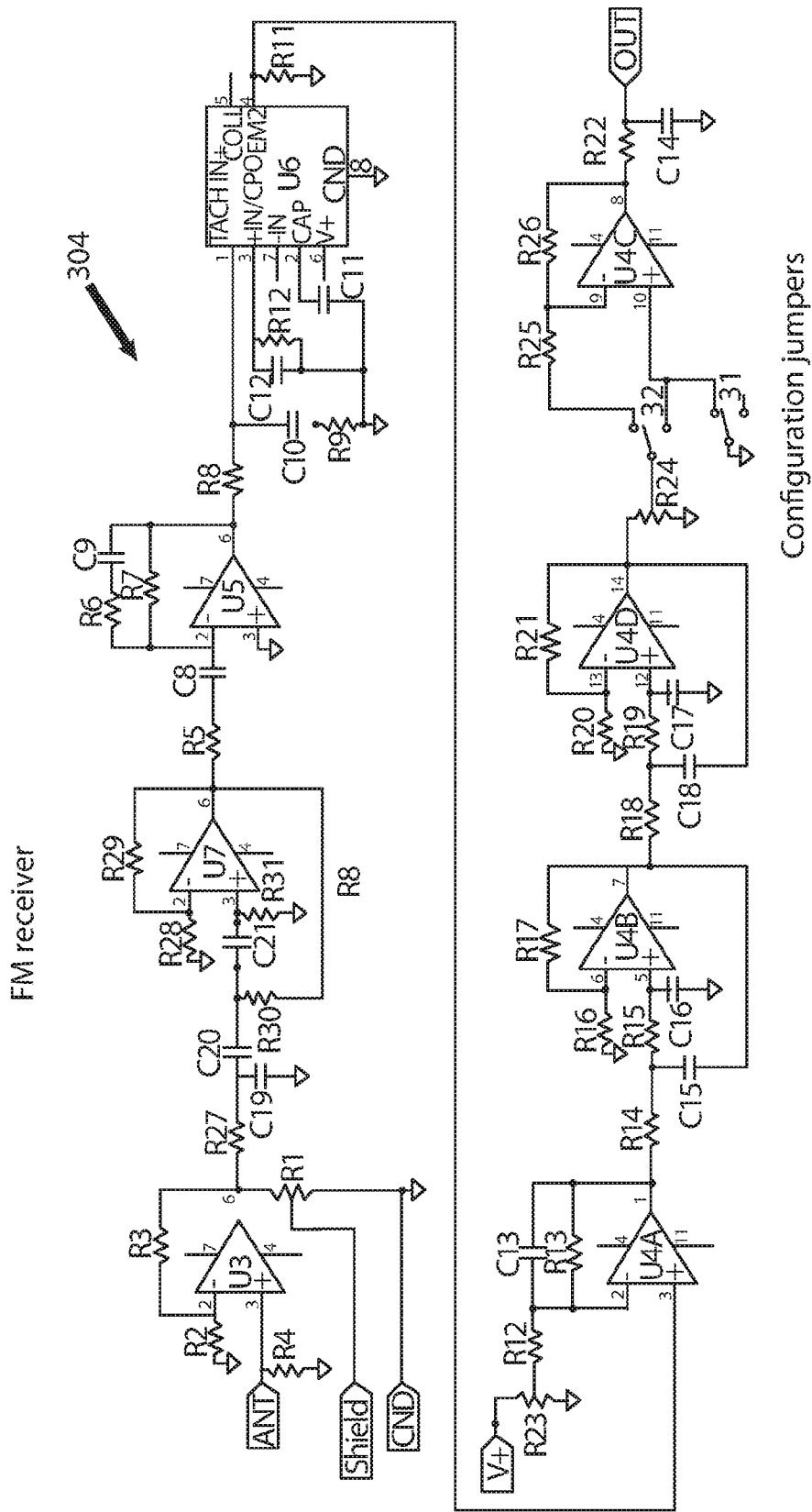
FIG. 3B illustrates one design of a single antenna high-impedance electric field receiver according to an aspect of the present invention.
Figure 4:
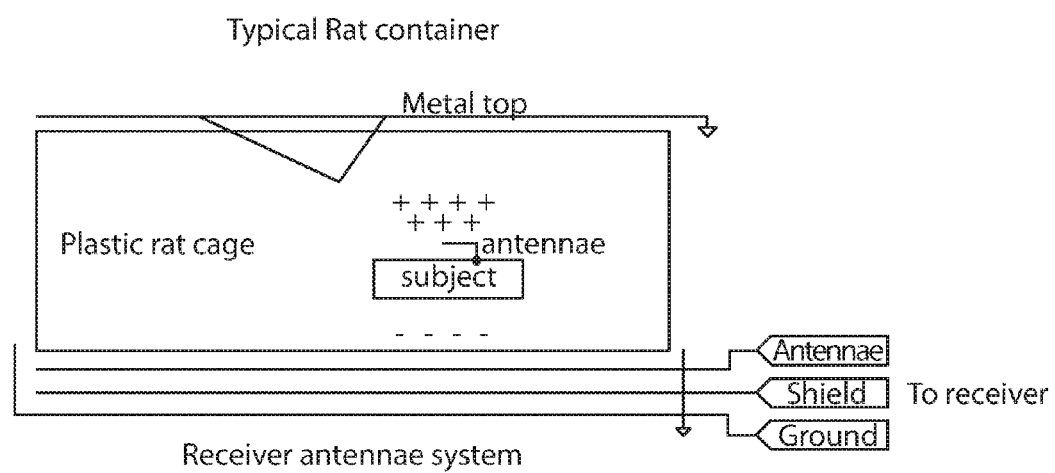
FIG. 4 illustrates an embodiment of a standard rat cage modified for capacitive-coupling of the transmitter and receipt of physiological data.

FIG. 3B illustrates a single channel receiver and amplifier 304 that can be used to receive the modulated signal from the transmitter. An exemplary IC U3, R2 and R3 (FIG. 3B) form an embodiment of a high-impedance amplifier with a gain of two. R4 is selected to match the antennae. The gain of two allows R1 to drive a capacitive isolation shield used in some applications. R27 and C19 form a 6 db/octave low-pass filter. U7, R28, R29, C20, R30, C21, and R31 form a 12 db/octave high-pass filter. U5 is an inverting amplifier with gain set by R7 and R5. C8, R6, and C9 form high and low pass poles.

U6 along with R8, C10, R9, C12, C11, and R11 form a frequency-to-voltage converter that converts the frequency modulated signal from the transmitter back to the original signal.

U4A, R23, C13, and R13 form a DC offset adjustment. U4B, R16, R17, R14, R15, C15, and C16 form a 12 Db/octave low pass filter. U4D, R18, R20, R21, R19, C18 and C17 form a 12 db/octave low pass filter.

All filter frequency points and amplifier gains vary depending on the application.

R24 adjusts gain. U4C, R25, and R26 with associated jumpers configure the gain and polarity of the output signal. R22 and C14 from a 6 db/octave low-pass filter.

Use of the Telemetry Device

Figure 8A:
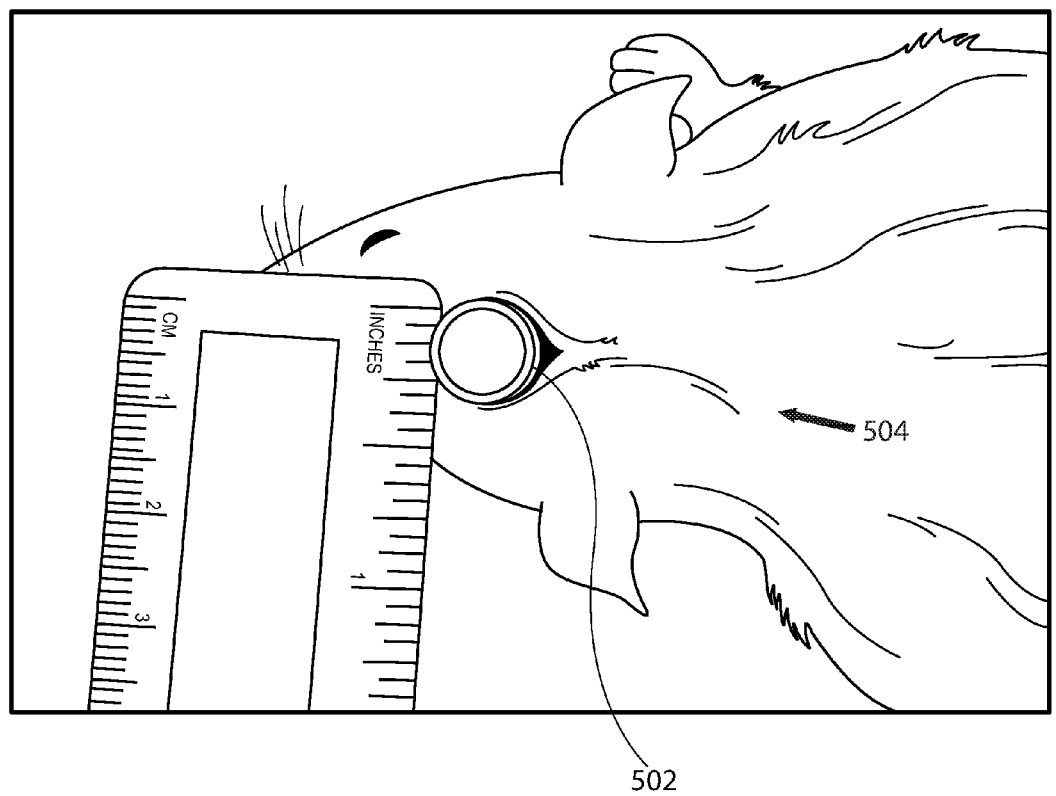
FIGS. 8A-11B illustrate aspects of embodiments of the transmitter device according to the present invention that transmits physiological signals to an antenna that is connected to an amplifier near the cage/shielding.
Figure 8B:
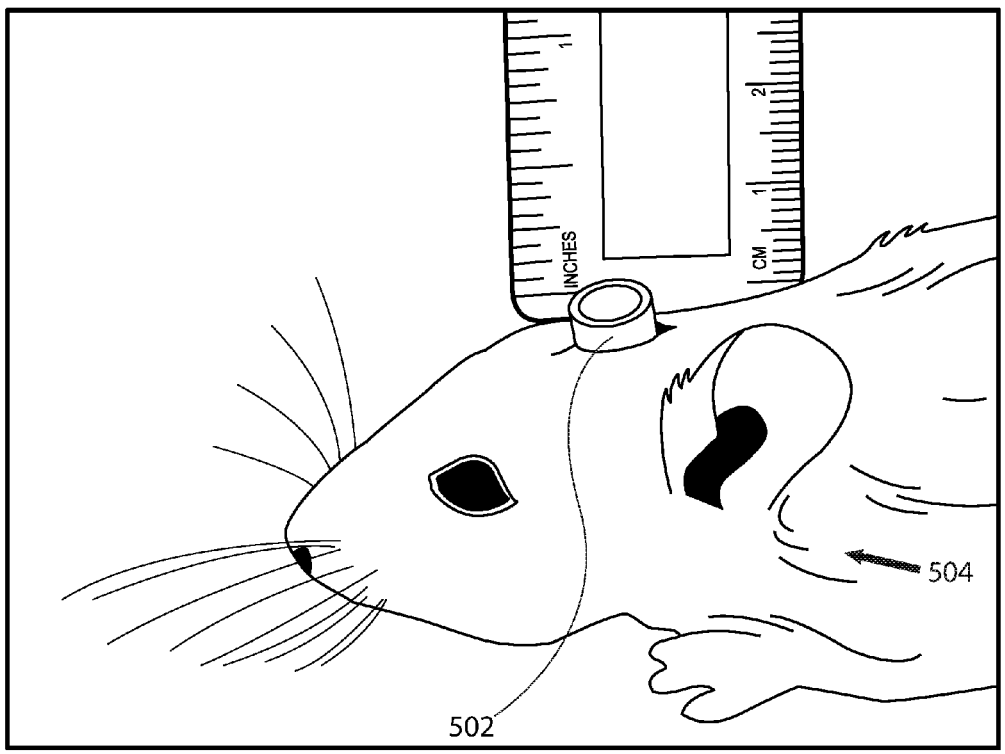
Figure 9A:
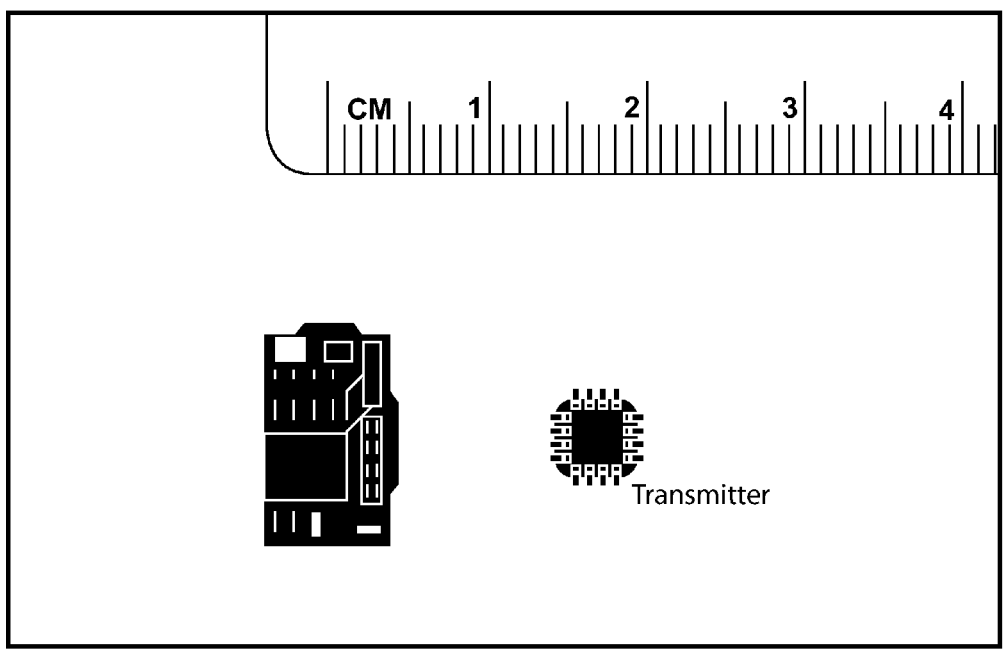
Figure 9B:
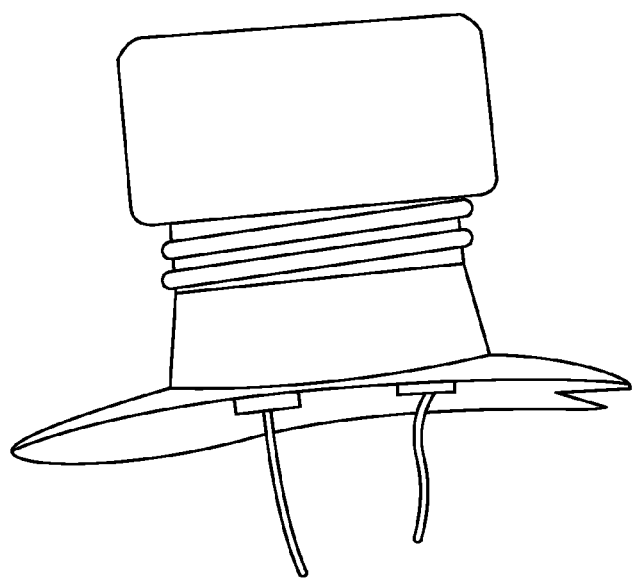
Figure 9C:
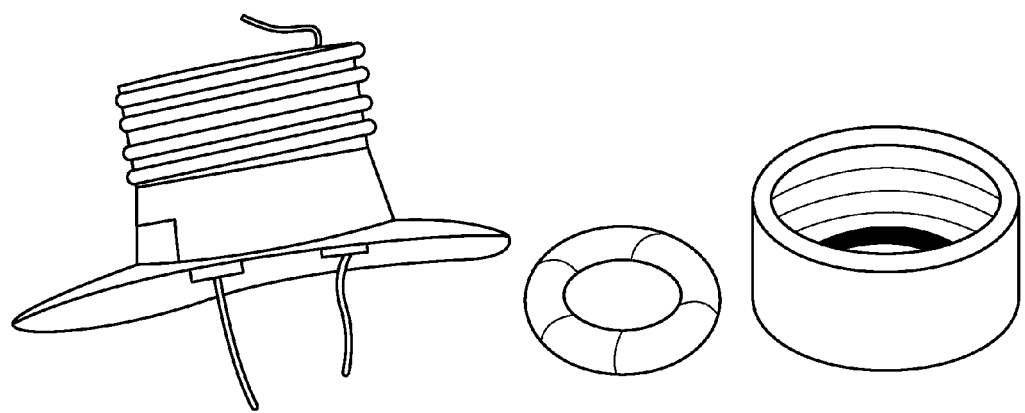
Figure 9D:
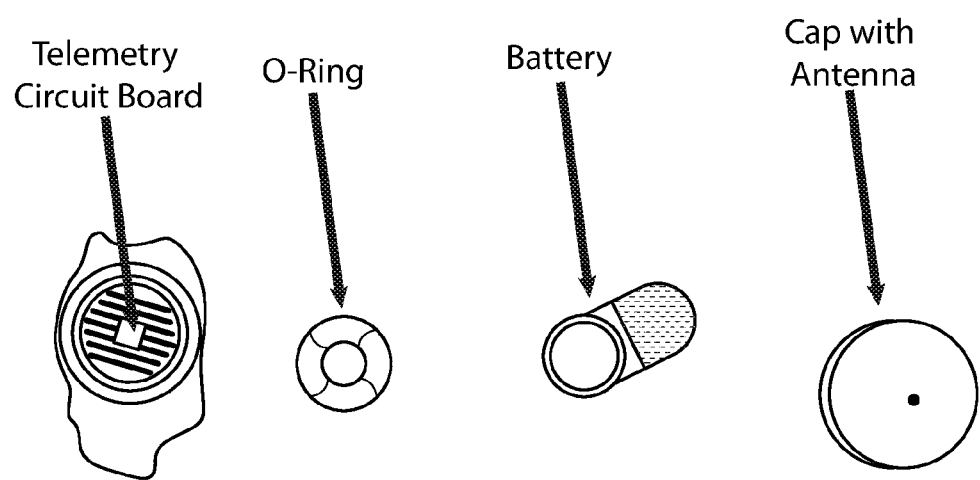
Figure 10:
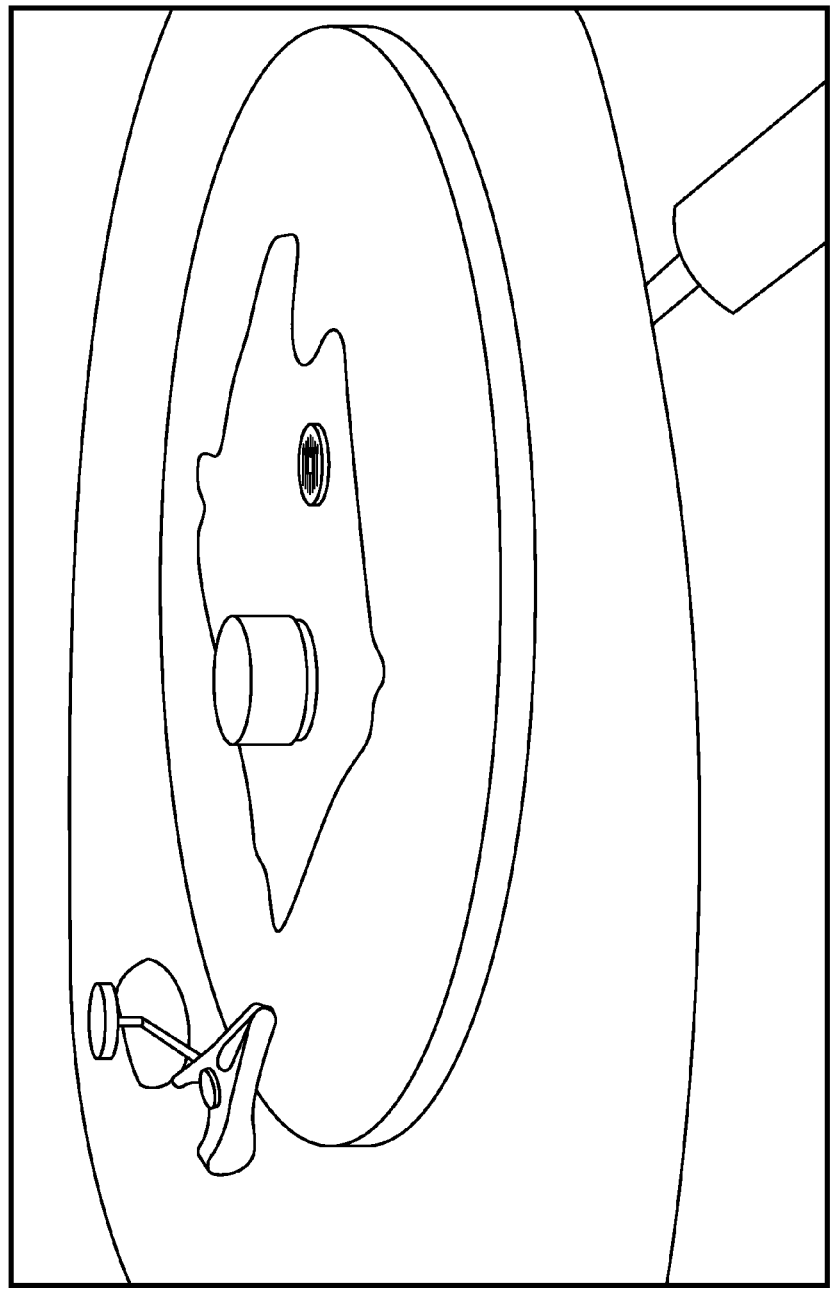
Figure 11A:
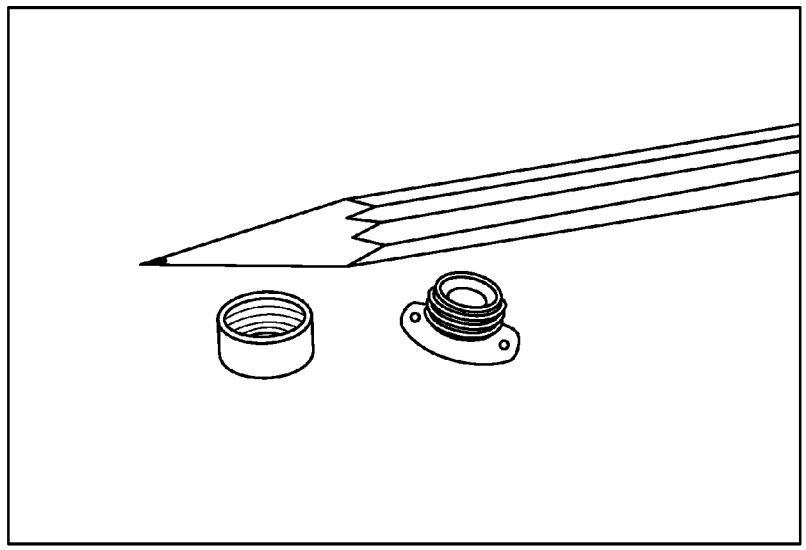
Figure 11B:
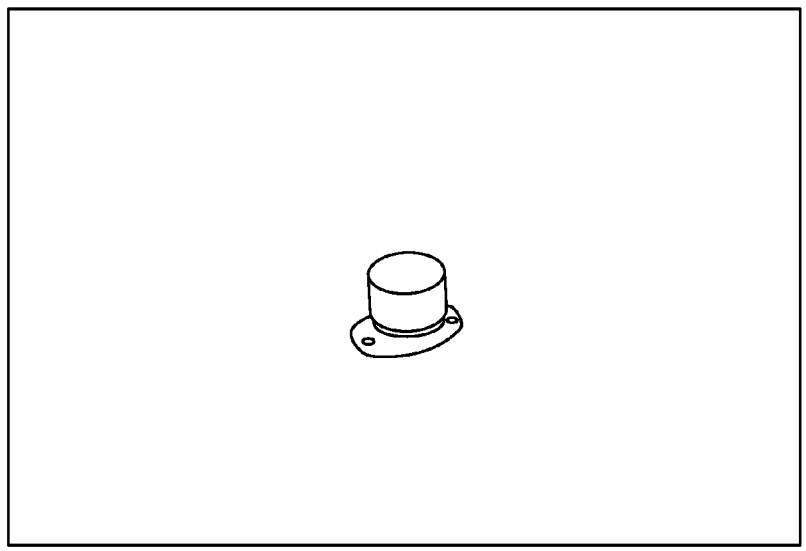

In one aspect, to record the EEG, an embodiment of the telemetry device 502 is implanted on the head of a laboratory animal 504 (e.g., a rat, FIGS. 5, 8A and 8B), that is housed in a standard animal cage 506 that is within a shielded enclosure 508. The telemetry device 502, which is only a few millimeters (FIGS. 8A-11B), transmits physiological signals 514 to an antenna 510 that is connected to an amplifier/receiver 512 near the cage/shielding.

Figure 12:
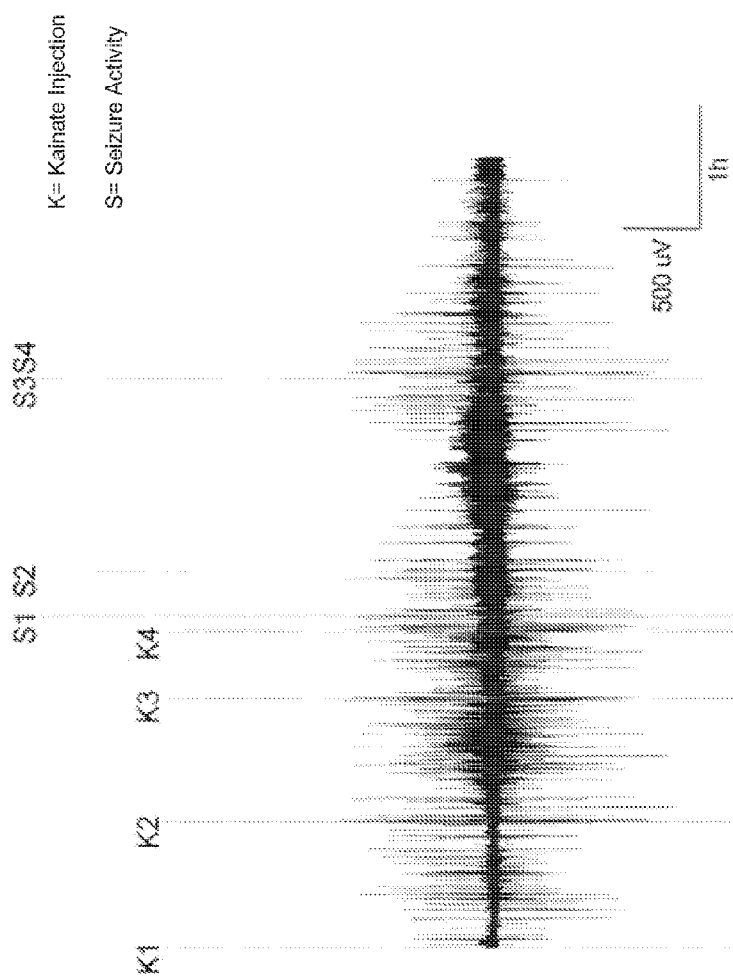
FIGS. 12 and 13 illustrate repetitive seizures induced in a rat treated with kainate.
Figure 13:
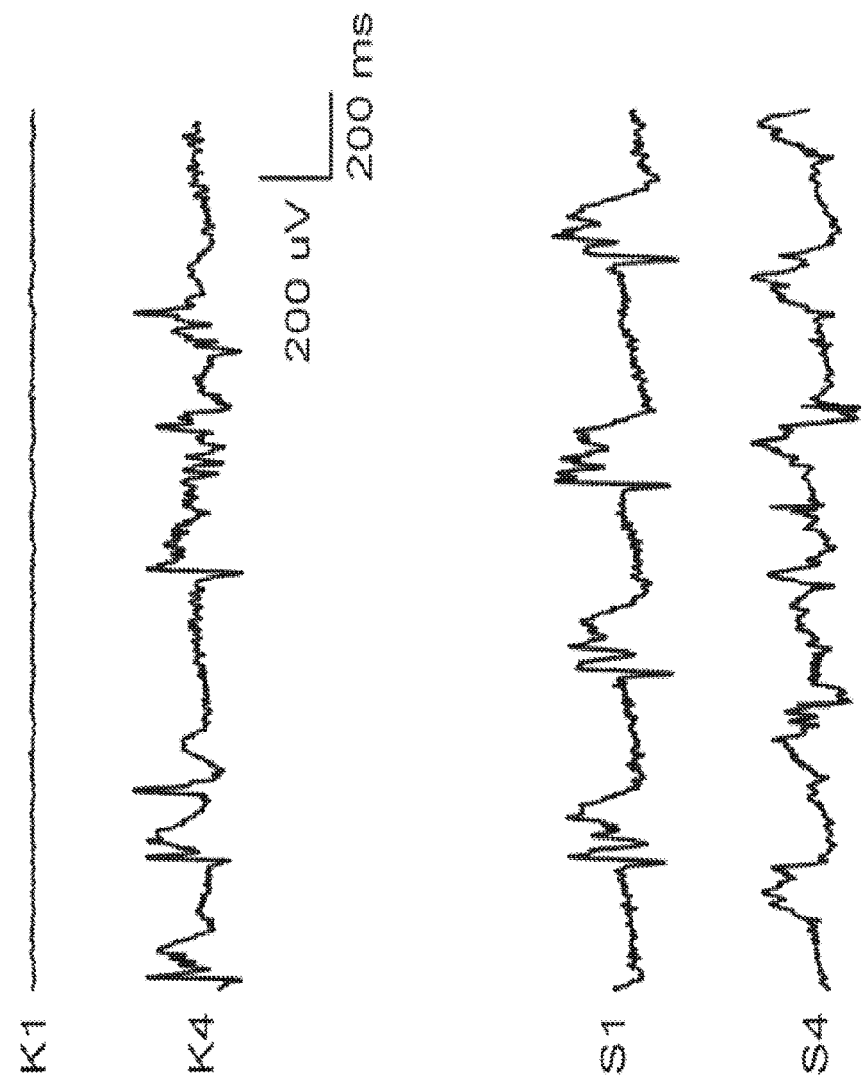

In an experiment, an embodiment of the device has been used to record electrophysiological signals 516 for weeks from a rat treated with kainate, which induces repetitive seizures (FIGS. 12 and 13). Since the kainate-induced status epilepticus involves repeated convulsive seizures, the likelihood that the telemetry device will remain operational during normal and even abnormal movement is high.

The recording device allows a myriad of physiological signals to be recorded from small experimental animals, particularly immature rats and mice. These recording procedures have been difficult if not impossible, but may become routine with variations of the proposed device. For example, embodiments according to the present invention allow the EEG to be recorded from small animals for chronic studies of epileptic seizures, which has important value in antiepileptic drug development. The EEG-recording device can also be useful for drug-development studies relating to promotion of sleep. A similar device can also be used for measurement of physiological signals from a small bird, as part of neuroscience research on the mechanisms of "bird song."

Figure 14:
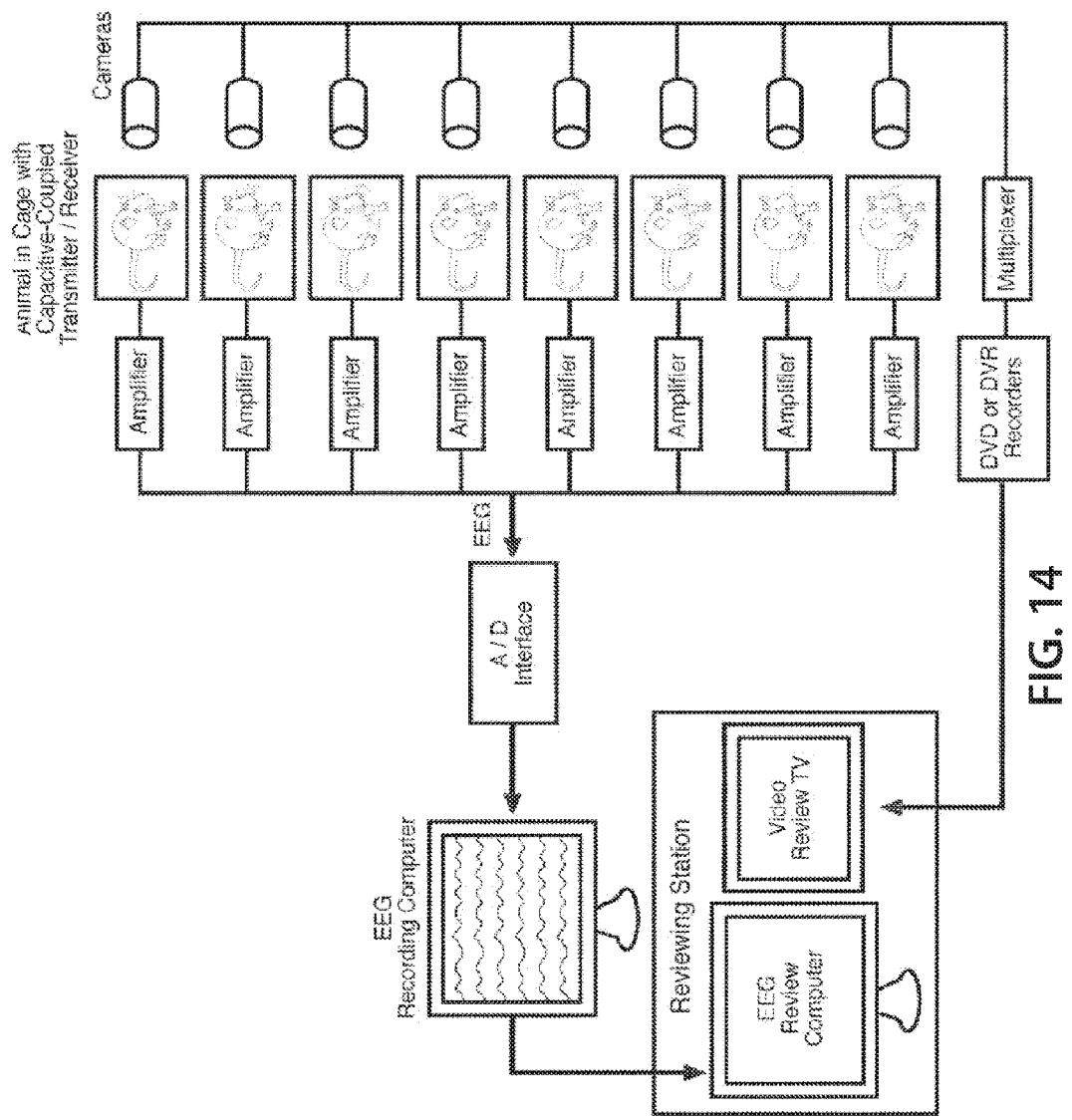
FIG. 14 illustrates an embodiment where multiple subjects can be simultaneously and continuously monitored for physiological activity as well as videoed.

In another aspect, as shown in FIG. 14, multiple subjects can be simultaneously and continuously monitored for physiological activity as well as videoed for physical activity.

Miniature RF Telemetry Device

Further described herein are embodiments of a miniature radio-frequency (RF) telemetry device to record, for example, electroencephalogram from persons with acute TBI, which allows remote monitoring and recording.

An embodiment of the device is comprised of a millimeter-sized EEG electrode/transmitter unit that wirelessly transmits EEG signals to a radio-frequency receiver connected to, for example, a laptop computer. The only component on the patient is a small electrode/transmitter unit. In one aspect, the device can be used to reliably detect acute TBI-associated seizures during a medical emergency both in transit to and within a field hospital setting. EEG telemetry strategies and techniques described herein provide prompt detection and continued monitoring of seizures under conditions where traditional ambulatory EEG is not feasible. In addition, this approach will have other uses in both military and civilian settings (e.g. easy, prompt seizure detection after field-exposure to nerve gas agents).

Described herein is an embodiment of a single-channel telemetry-based EEG device that will allow detection of electrographic seizures in an emergency medical setting. It is to be appreciated that several independent channels can be used simultaneously. The device uses a pair of small EEG electrodes coupled with a miniature telemetry-based recording/transmitter system that will allow acquisition and storage of EEG data on a computing device such as the one described in relation to FIG. 1, above. A USB A/D acquisition hardware, laptop PC, and chart recorder/storage software can be used in coordination with the device, including analysis of received data by analysis software and transmission of received data over a network (e.g., the Internet) for review and/or further analysis by trained medical personnel or analysis software.

Figure 15:
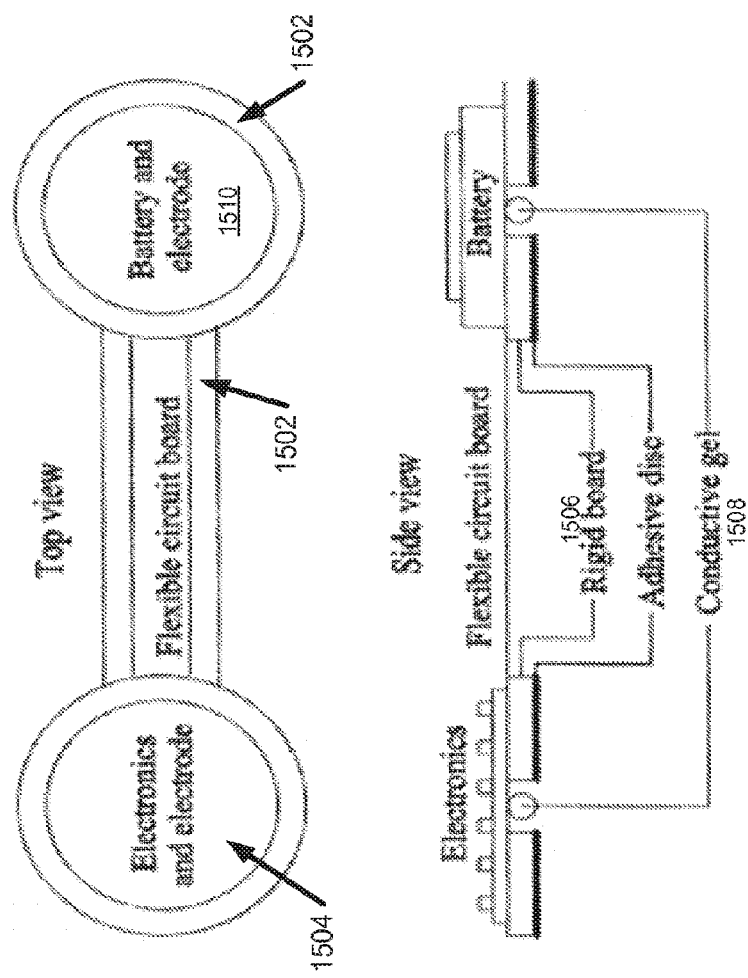
FIG. 15 is a schematic diagram of the top and side views of an embodiment of the EEG telemetry device.

Described below is a small, lightweight transmitter that can be easily mounted on a human skull. In one embodiment, characteristics of an exemplary transmitter include a transmitting radius of about 50 feet, a battery life with, for example, a 3 volt lithium 1632 cell (125 MAH) of at least about 24 hours, and a bandwidth of approximately 0.1 to 300 Hz. FIG. 15 illustrates an embodiment of the device. FIG. 15 is a schematic diagram of the top and side views of an embodiment of the EEG telemetry device. As above, it is also to be appreciated that several such transmitters can be used simultaneously to monitor a single subject.

The embodiment of FIG. 15 can be constructed on a substrate 1502 such as a flexible circuit board with built-in EEG or other physiological recording electrodes and/or environmental sensors 1504 attached to both ends. In one aspect, the substrate is a single piece of material. In one aspect, the antenna can be incorporated into the flexible circuit board. The flexible circuit board can be, in one example, approximately 0.008" thickness. The rigid board 1506, as shown on FIG. 15, can, in one example, be 0.02" thickness. Each electrode can have a region for conductive gel 1508 to connect the two electrodes to the scalp or other body part. One electrode has a battery 1510 on the opposite side, and the other has the transmitter electronics on the opposite side. The device is designed to have a low profile so that it will not be easily dislodged or be uncomfortable to an awake individual. In one aspect, embodiments according to this device provide rapid detection of non-convulsive seizures after TBI and allow early, monitor-directed anti-seizure therapy.

Transmitter

Figure 16:
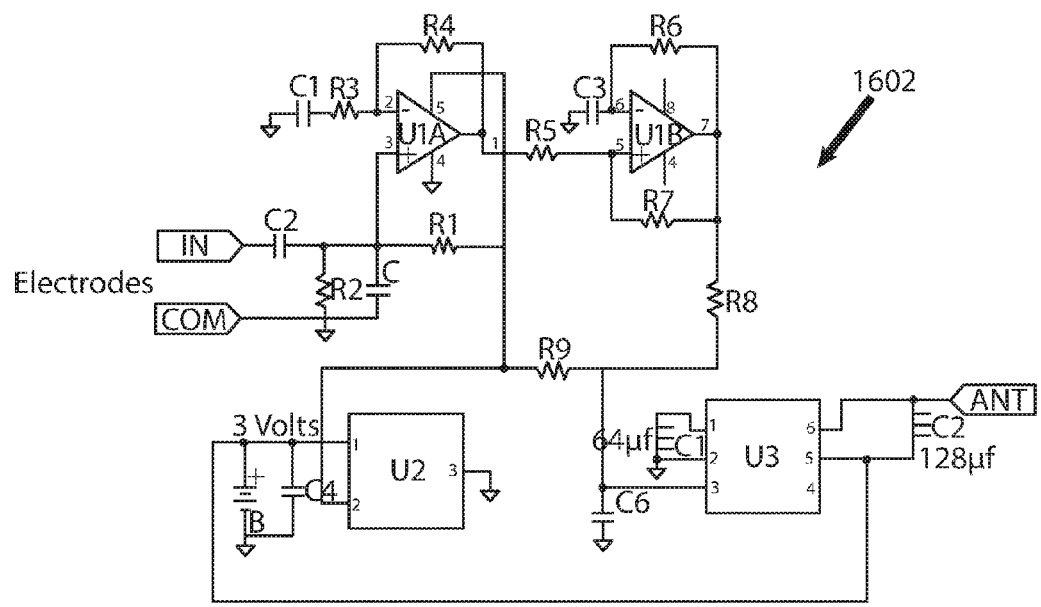
FIG. 16 is an illustration of a RF FM EEG transmitter according to the present invention.

FIG. 16 is an illustration of a RF FM EEG transmitter 1602 according to the present invention. In this embodiment, U1 is a MCP6142 dual operational amplifier in a MSOP surface mount package. It is biased at one-half of U2's output by divider R1 and R2. The EEG signal is AC coupled through C2 to U1A. Gain is set with R4/R3 and low frequency response set by C1. U1B is a square wave oscillator with frequency set by R6 and C3. R5 coupled to U1A-1 sets the pulse width at about 50% for both positive and negative saturation times of U1B. Resistor R5 also modulates the pulse width duration of U1B with the signal waveform from U1A. The non-linear properties between the rise and fall times of U1B provide significant frequency modulation allowing an FM type receiver to be used. U2 is a precision voltage reference providing approximately 1.247 volts from the 3 volt lithium cell "B". This powers U1 for stable operation and sets the center operating frequency of U3 through R9. R8 couples the FM oscillator U1B to modulate RF oscillator/amplifier U3. LI sets center frequency of U3, L2 is a "pull up" for the open collector output of U3. U3 as shown operates at approximately 234.275 megahertz. However, the FCC allows power levels below 10 dbm on some parts of the FM band. Embodiments of the current transmitter produce about −21 dbm into 50 ohms, and is tunable from 40 to 450 MHz. Therefore frequency bands between 40 and 450 MHz that are not otherwise used, and are available for the telemetry transmission system, are within the scope of embodiments of this invention.

Receiver

In one aspect, an FM wideband receiver (e.g., a ICOM IC-R5 receiver) is used to pick up the RF signal from the transmitter. The audio output is then fed to bandwidth limits and a frequency to voltage converter (similar to FIG. 3B) to recover the original EEG signal.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and systems. Efforts have been made to ensure accuracy with respect to numbers (e.g., amounts, temperature, etc.), but some errors and deviations should be accounted for.

In one example, aspects according to the present invention can be used for at-home, untethered, longer-term monitoring of a patient post-TBI and early prediction and treatment of seizure activity. Further examples of use include immediate detection of EEG activity soon after a TBI and proscribed treatment predicated on such activity. Another use is to monitor patients that have experienced a single seizure. In many instances, such a patient should not or cannot drive for weeks or months until it is clear that the patient has not experienced another seizure. Yet another use would be to help patients with intractable epilepsy obtain more reliable measures of their seizure frequency and severity, since these individuals are often amnesic after a seizure and thus self-reporting is generally inaccurate. Embodiments of the miniature telemetry device described herein can be used to determine whether the patient has or has not experienced another seizure. Embodiments according to the invention can also be used for remote monitoring of EEG activity in various situations.

Figure 17:
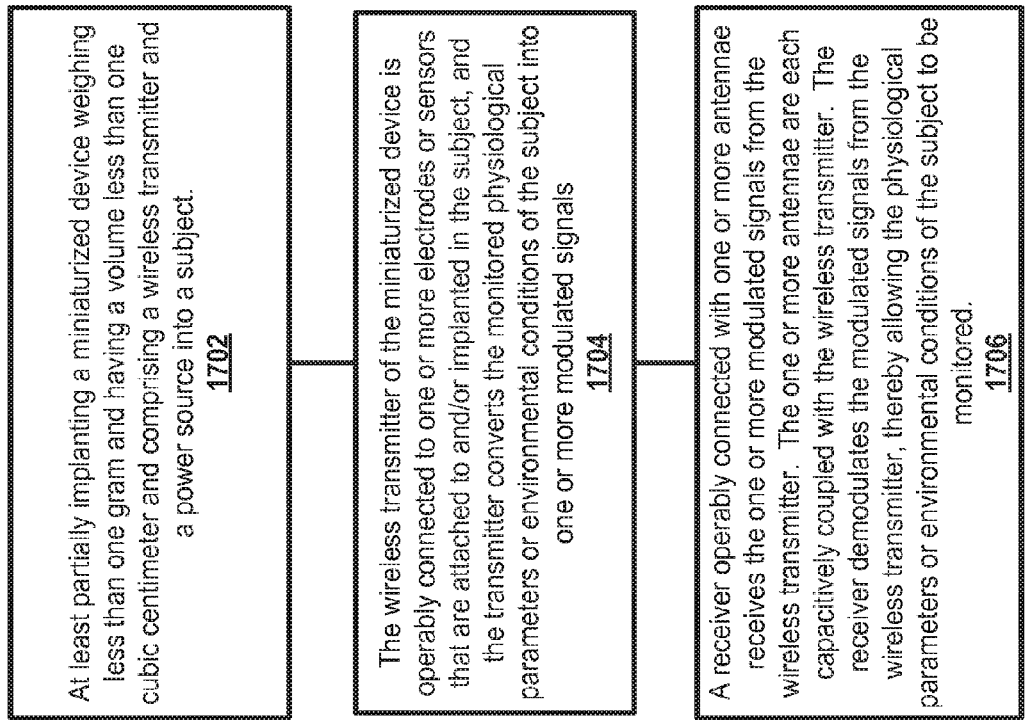
FIG. 17 is a flowchart illustrating a method of wireless biomedical telemetry.

FIG. 17 is a flowchart illustrating a method of wireless biomedical telemetry. The exemplary process comprises step 1702, at least partially implanting a miniaturized device weighing less than one gram and having a volume less than one cubic centimeter and comprising a wireless transmitter and a power source into a subject. The subject can be a laboratory animal such as a rat or a mouse, or can be a human. The miniaturized device is at least partially implanted into the subject with minimally invasive procedures and at least a portion of the miniaturized device is external to the subject. The wireless transmitter of the miniaturized device is operably connected to one or more electrodes or sensors that are attached to and/or implanted in the subject. At step 1704, the transmitter converts monitored physiological parameters or environmental conditions of the subject into a modulated signal. At step 1706, a receiver operably connected with one or more antennae receives the modulated signal from the wireless transmitter. The one or more antennae are each capacitively coupled with the wireless transmitter. The receiver demodulates the modulated signals from the wireless transmitter, thereby allowing the physiological parameters or environmental conditions of the subject to be monitored.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method inventive concept does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following inventive concepts.

The invention claimed is:

1. A wireless biomedical telemetry system comprising:
   at least one detector for attachment to a living subject, the living subject movable in multiple directions relative to or on a substrate within a preselected volume, said at least one detector being configured to detect a signal generated by said living subject and to generate a detector signal reflective of the signals detected; and
   a telemetry device for attachment to and external to said living subject, said telemetry device including a power source and a wireless transmitter, said wireless transmitter being operably connected to said power source to receive power therefrom and to said at least one detector to receive said detector signal, and said wireless transmitter being configured to generate a modulated signal based on said detector signal;
   a transmitting antenna connected to said wireless transmitter for receiving the modulated signal, said transmitting antenna with said living subject and the free space in said volume configured to wirelessly transmit said modulated signal through said free space said transmitting antenna being movable with said living subject relative to or on said substrate; and
   a receiving antenna sized and fixedly positioned away from said living subject to effect a capacitive coupling with said transmitting antenna to receive through said free space said modulated signal therefrom;
   a receiver connected to said receiving antenna and configured to demodulate said modulated signal to form receiving signals reflective of the signals generated by said living subject; and a computer connected to said receiver configured to receive and selectively store data reflective of said signals generated by said living subject and display images reflective of said signals generated by said living subject.

2. The system of claim 1, wherein the detector includes an electrode.

3. The system of claim 1, wherein the power source comprises one or more photodiodes.

4. The system of claim 1, wherein the signals generated by said living subject includes at least one of an EEG, an ECG, blood pressure, temperature and blood pressure signals.

5. The system of claim 1, wherein the living subject is one of a rat, a mouse, a bird, and a human.

6. The system of claim 1, wherein the receiving antenna is fixedly positioned.

7. The system of claim 6, further comprising a ground plane and a capacitive isolation shield located between said receiving antenna and the ground plane, wherein the receiving antenna is planar and the distance between the receiving antenna and the ground plane is controlled.

8. The system of claim 7, wherein said at least one detector, said telemetry device and said transmitting antenna are physically associated with a circuit board sized smaller than the head of said living subject, and wherein the circuit board includes a substrate that is flexible to conform to the living subject.

9. The system of claim 8, wherein said flexible circuit board is sized for attachment to an area of the living subject that is less than about 2 square centimeters.

10. The system of claim 8, wherein said free space is filled with a gas.

11. The system of claim 8, wherein said flexible circuit board, said detector, said telemetry device and said transmitting antenna together weigh less than about 2 grams.

12. The system of claim 10, wherein said gas is air.

13. The system of claim 10, wherein said flexible circuit board, said detector, said telemetry device and said transmitting antenna together weigh less than about 1 gram.

14. A method of wireless biomedical telemetry comprising:
providing a detector configured for detecting at least one signal generated by a living subject variably spaced from or on a substrate within a volume;
attaching said detector to said living subject;
operating said detector to generate a detector signal reflective of said signals detected as said living subjects moves within said volume;
providing and operating a telemetry device for attachment to and external to said living subject, said telemetry device including a power source, a wireless transmitter and an antenna,
said wireless transmitter being operably connected to said power source to receive power therefrom and to said detector, said wireless transmitter being operable to generate a modulated signal reflective of said detector signal, said antenna being connected to said wireless transmitter for receiving said modulated signal, and said antenna being movable in multiple directions relative to and on said substrate with said living subject; and
providing a receiving antenna capacitively coupled with said living subject and transmitter to receive said wireless transmission from said transmitting antenna, said receiving antenna being spaced from said living subject and connected to a receiver; and
providing a receiver and connecting said receiver to said receiving antenna to receive said wireless transmission therefrom; and
operating said receiver to demodulate said wireless transmission to form receiving signal reflective of the signal generated by said living subject.

15. The method of claim 14, wherein the detector includes an electrode.

16. The method of claim 14, further comprising: providing a computer having a computer readable memory, said computer being connected to receive said receiving signals and storing in computer-readable memory at least one of the detector signal, the modulated signal and the demodulated signal.

17. The method of claim 16, wherein the power source comprises one or more photodiodes.

18. The method of claim 17, wherein the signals generated by said living subject include at least one of EEG, ECG, blood pressure, temperature and blood pressure signals.

19. The method of claim 14, wherein the living subject is one of a bird, a human, a rat and a mouse.

20. The method of claim 14, wherein the receiving antenna is fixed relative to said living subject.

21. The method of claim 20, wherein the receiving antenna is planar and further comprises a ground plane and a capacitive isolation shield located between said receiving antenna and the ground plane and the distance between the receiving antenna and the ground plane is controlled.

22. The method of claim 17, wherein the at least one detector, the telemetry device and the transmitting antenna are physically associated with a circuit board, and wherein the circuit board includes a substrate that is flexible to conform to the living subject and wherein said circuit board is sized to be less than 2 square centimeters and to be less than 2 grams in weight.

23. The method of claim 22, further comprising:
providing an adhesive for adhesively attaching the flexible circuit board to the living subject.

24. A wireless biomedical telemetry system for use with a living subject, said biomedical telemetry system comprising:
an enclosure defining a volume and having at least one substrate, said volume being sized to contain a living subject variably spaced from or on said substrate, said enclosure including a capacitive isolation shield proximate said substrate;
detector configured for attachment external to said living subject, said detector being configured to detect a signal generated by said living subject and to generate a detector signal reflective of the signal detected;
a circuit board for attachment proximate to said detector, said circuit board including a power source, telemetry device including a power source and a wireless transmitter mechanically attached to a substrate to form a circuit board, said wireless transmitter being connected to said power source to receive power therefrom, and said wireless transmitter being connected to each of said at least one detectors to receive said detector signal therefrom and to generate a modulated signal based on said detector signal;
a transmitting antenna connected to said wireless transmitter for receiving the modulated signal, said transmitting antenna forming with said living subject a capacitor for wireless capacitive coupling to effect wireless transmission through a gas of said modulated signal, said first transmitting antenna being movable with said living subject in multiple directions relative to said substrate; and a receiving antenna sized and formed to receive through said gas said modulated signal;

a receiver connected to said receiving antenna and configured to demodulate said modulated signal to form receiving signals reflective of the signals generated by said living subject; and a computer connected to said receiver to receive and selectively store data reflective of said signals generated by said living subject and display images reflective of said signals generated by said living subject.

* * * * *

UNITED STATES PATENT AND TRADEMARK OFFICE
CERTIFICATE OF CORRECTION

PATENT NO.       : 9,474,461 B2
APPLICATION NO.  : 12/681408
DATED            : October 25, 2016
INVENTOR(S)      : John H. Fisher et al.

It is certified that error appears in the above-identified patent and that said Letters Patent is hereby corrected as shown below:

In the Specification

Column 1, Line 11, "This invention is made with government support under grant numbers NS045144, NSO49620, NSO42359, DC004390 and DC006876 awarded by National Institute of Health. The government has certain rights to this invention." should read -- This invention is made with government support under grant numbers NS045144, NS049620, NS042359, DC004390 and DC006876 awarded by National Institute of Health. The government has certain rights to this invention. --.

In the Claims

Claim 24, Column 16, Line 47, "detector configured for attachment external to said living..." should read -- a detector configured for attachment external to said living... --.

Signed and Sealed this
Second Day of May, 2017

Michelle K. Lee
*Director of the United States Patent and Trademark Office*